(12) United States Patent
Hulbert

(10) Patent No.: US 10,583,904 B2
(45) Date of Patent: *Mar. 10, 2020

(54) EMERGENCY DETECTION AND ASCENT DEVICE FOR A DIVER

(71) Applicant: Christopher B. Hulbert, Winnetka, IL (US)

(72) Inventor: Christopher B. Hulbert, Winnetka, IL (US)

(73) Assignee: Christopher B. Hulbert, Winnetka, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/164,295

(22) Filed: Oct. 18, 2018

(65) Prior Publication Data

US 2019/0054989 A1     Feb. 21, 2019

Related U.S. Application Data

(63) Continuation of application No. 15/489,463, filed on Apr. 17, 2017, now Pat. No. 10,131,412.

(Continued)

(51) Int. Cl.
*B63C 11/26* (2006.01)
*A61B 5/00* (2006.01)
(Continued)

(52) U.S. Cl.
CPC ............ *B63C 11/26* (2013.01); *A61B 5/0205* (2013.01); *A61B 5/02416* (2013.01);
(Continued)

(58) Field of Classification Search
CPC . B63C 11/26; B63C 11/2236; B63C 11/2245; B63B 22/06; B63B 22/18;
(Continued)

(56) References Cited

U.S. PATENT DOCUMENTS

| 5,156,055 A | 10/1992 | Hollis et al. |
| 5,889,730 A | 3/1999 | May |

(Continued)

FOREIGN PATENT DOCUMENTS

GB         2304444 A         3/1997

OTHER PUBLICATIONS

"Fitbit Surge"—Fitness Super Watch, Product Manual Version 1.2, (circa 2014) 48 pages.
"Fitbit Charge 2"—Product Manual, Version 1.0 (2016), 42 pages.

*Primary Examiner* — Anthony D Wiest

(57) ABSTRACT

An apparatus is disclosed having a sensor configured to measure a biological parameter of a diver and transmit a sensor signal. A controller is configured to determine that the biological parameter value correlated to the sensor signal is anomalous and responsively issue a rescue deployment signal to a buoyancy valve assembly. The buoyancy valve assembly has an inlet port connectable to a source of pressurized gas and an outlet port connectable to a buoyancy control bladder. The buoyancy valve assembly configured to receive the rescue deployment signal and responsively supply pressurized gas from the inlet port to the outlet port and buoyancy bladder, whereby the diver may ascend the water surface, even if disabled.

6 Claims, 14 Drawing Sheets

Related U.S. Application Data

(60) Provisional application No. 62/458,229, filed on Feb. 13, 2017.

(51) Int. Cl.

| | | |
|---|---|---|
| *B63C 11/22* | (2006.01) | |
| *A61B 5/024* | (2006.01) | |
| *A61B 5/0205* | (2006.01) | |
| *A61B 5/08* | (2006.01) | |
| *A61B 5/1455* | (2006.01) | |
| *G08B 5/00* | (2006.01) | |
| *G08B 21/04* | (2006.01) | |
| *G08B 21/08* | (2006.01) | |
| *G08B 25/01* | (2006.01) | |
| *B63B 22/06* | (2006.01) | |
| *B63B 22/18* | (2006.01) | |
| *G08B 21/02* | (2006.01) | |
| *B63C 11/02* | (2006.01) | |

(52) U.S. Cl.
CPC ........ *A61B 5/02438* (2013.01); *A61B 5/0816* (2013.01); *A61B 5/14551* (2013.01); *A61B 5/742* (2013.01); *A61B 5/746* (2013.01); *B63B 22/06* (2013.01); *B63B 22/18* (2013.01); *B63C 11/2236* (2013.01); *B63C 11/2245* (2013.01); *G08B 5/002* (2013.01); *G08B 21/0453* (2013.01); *G08B 21/088* (2013.01); *G08B 25/016* (2013.01); *A61B 2503/10* (2013.01); *A61B 2560/0242* (2013.01); *B63B 2730/00* (2013.01); *B63C 2011/021* (2013.01); *G08B 21/02* (2013.01)

(58) Field of Classification Search
CPC ... B63B 2730/00; A61B 5/14542; A61B 5/08; A61B 5/02438
USPC .................................................. 405/185, 186
See application file for complete search history.

(56) References Cited

U.S. PATENT DOCUMENTS

| | | |
|---|---|---|
| 6,592,298 B2 | 7/2003 | Beltrani |
| 7,272,075 B2 | 9/2007 | Pope |
| 7,303,453 B1 | 12/2007 | Bourke |
| 7,310,549 B1 | 12/2007 | Angelini et al. |
| 7,797,124 B2 | 9/2010 | Hollis et al. |
| 8,417,351 B2 | 4/2013 | Kilger |
| 9,339,237 B2 | 5/2016 | Frix et al. |
| 9,339,242 B2 | 5/2016 | Bailey et al. |
| 9,404,600 B2 | 8/2016 | Kainuma et al. |
| 2010/0167608 A1 | 7/2010 | Daye et al. |
| 2012/0128425 A1 | 5/2012 | Walck |
| 2013/0259579 A1 | 10/2013 | Bonzon et al. |
| 2014/0167984 A1 | 6/2014 | Holopainen et al. |
| 2015/0216454 A1 | 8/2015 | Kasahara et al. |
| 2016/0355245 A1* | 12/2016 | Schechter ............... B63C 11/08 |

* cited by examiner

EMERGENCY DETECTION AND ASCENT DEVICE FOR A DIVER

CLAIM FOR PRIORITY TO RELATED APPLICATIONS

This application is a continuation application of U.S. application Ser. No. 15/489,463, filed on Apr. 17, 2017, which claims priority to U.S. Provisional Application No. 62/458,229, filed on Feb. 13, 2017. The contents of the two applications are incorporated herein.

BACKGROUND

Technical Field

The present system relates to the field of underwater diving and, more particularly, to safety devices used while diving.

Background Art

Underwater diving typically involves a diver breathing from a source of compressed gas. A typical scuba tank for a recreational driver holds gas (e.g., air) at a relatively high pressure (such as 3,000 pounds per square-inch (psi)). The tank is often held by a buoyancy control device (BCD), also referred to as a buoyancy compensator or stabilizer. During use, the BCD is strapped onto the back of a scuba diver.

In a typical single-hose, open-circuit, two-stage scuba system, a first regulator stage reduces the gas pressure in the tank to a low pressure of, for example, 120 to 150 psi. A hose typically supplies gas at the low pressure to a valve on the BCD. The valve allows a diver to inject gas from the tank into one or more bladders in the BCD or to release air from the BCD into the water. In this way, the diver can control her buoyancy, often striving for neutral buoyancy during a dive and positive buoyancy (i.e., a supernatant condition) while ascending toward, or swimming on, the water surface.

Gas at the low pressure is also supplied by a hose to a second stage of the regulator, which is held by a diver's mouth. The second stage of a demand-valve regulator delivers breathable gas (e.g., air) at approximately ambient pressure to the diver's mouth or full-face mask. The ambient pressure, of course, depends of the water depth of the diver.

Another example of underwater diving equipment includes "Snuba" (a combination of the words, snorkel and scuba), which allows underwater diving with air supplied from the water surface. Instead of coming from a tank strapped to a diver's back, air is supplied to the second stage of the regulator from long hose connected to a compressed air tank at the water surface, held by a flotation device.

Upon occasion, an underwater diver encounters difficulty and should promptly ascend toward the water surface and/or summon help. For example, nitrogen narcosis (also sometimes referred to as "the martini effect") can arise from breathing nitrogen at an elevated pressure (i.e., at substantial depth). It can impair a diver's judgment, coordination, and ability to focus mentally.

If, through inattention or the effects of nitrogen narcosis, a diver breathing air descends too deeply in the water, the diver can suffer from oxygen poisoning (as a result of breathing oxygen at too high a partial pressure).

For deeper dives, a diver may use a "non-air" gas mixture. A commercial scuba diver going to depths of 300 or more feet may use, e.g., 10 different bottles, with different combinations of gasses being supplied to the diver at different depths. If the diver's computerized valve assembly malfunctions (e.g., sea water seeps into the computer housing and degrades the performance of the valve controller), the diver must be able promptly to adjust the tank valves manually, a sometimes difficult task.

Divers at remote dive locations may sometimes have their tanks filled locally, near the dive site. On such occasions, a compressor, powered by a gasoline engine, may be used to pump air into the dive tanks. If the compressor operator is not careful, exhaust gas from the gasoline engine, including carbon monoxide, may be pulled in by the air compressor and pumped into a tank. Carbon monoxide is colorless, tasteless, odorless, and toxic.

Decompression sickness (also known as the bends or Caisson Disease) can affect a diver who surfaces too quickly. Upon descending in the water, the pressure around the diver increases, causing nitrogen to be absorbed into her body tissue. To release the nitrogen slowly from her body, a diver generally should ascend slowly and sometimes carry out decompression, or safety, stops. This allows the nitrogen to seep out of the body tissue slowly. If a diver ascends too quickly, however, there can be a build-up of nitrogen bubbles in the diver's body, adversely affecting the diver. A diver who is injured or otherwise under stress may encounter difficulty in ascending at a proper rate or following a desirable dive profile (including safety stops).

Of course, a diver may, at any time, experience an adverse health issue, such as a stroke or heart attack, requiring prompt medical attention. A muscle cramp (such as a debilitating stomach cramp) can pose a risk to a diver.

SUMMARY

The present disclosure describes implementations that relate to a safety system for underwater divers. In one example implementation, the present disclosure describes a sensor and alarm. The sensor detects an anomalous condition and issues an alarm, such as, for example, an audible alarm or a flashing light or both. Upon determining that a major anomaly exists and that rescue measures are enabled, the system inflates a bladder, such as those on a diver's BCD, bringing her toward the water surface.

In another example implementation, upon determining that a major anomaly exists and that rescue measures are enabled, the system releases a buoy, allowing it to float to the water surface. The buoy issues an alarm for others on the surface.

In still another example implementation, the buoy is tethered to the diver. The tether allows a rescue diver to follow the tether to the diver in distress. In another example implementation, the tether enables data transmission, so that the diver may talk, or otherwise communicate with, others on the surface.

The foregoing summary is illustrative only and is not intended to be limiting. In addition to the illustrative aspects, implementations, and operations described above, further aspects, implementations, and operations will become apparent by reference to the figures and the following detailed description.

DETAILED DESCRIPTION

Generally

The following detailed description describes various aspects, implementations, and operations of the disclosed system with reference to the accompanying figures. The illustrative aspects, implementations, and operations described herein are not meant to be limiting. It is contemplated that certain aspects of the disclosed system can be arranged and combined in a wide variety of different configurations.

Unless context suggests otherwise, the features illustrated in each of the figures may be used in combination with one another. Thus, the features should be generally viewed as component aspects of one or more overall implementations, with the understanding that not all illustrated features are necessary for each implementation.

Any enumeration of elements, blocks, or steps in this disclosure or in any associated claim is for purposes of clarity. Thus, such enumeration should not be interpreted to require or imply that these elements, blocks, or steps adhere to a particular arrangement or are carried out in a particular order.

By the terms, "substantially," "approximately," or "generally," it is meant that the recited characteristic, parameter, or value need not be achieved exactly, but that deviations or variations, including for example, tolerances, measurement error, measurement accuracy limitations, and other factors known to those of ordinary skill in the pertinent art may occur in amounts that do not preclude the effect the feature was intended to provide.

Figure 1:
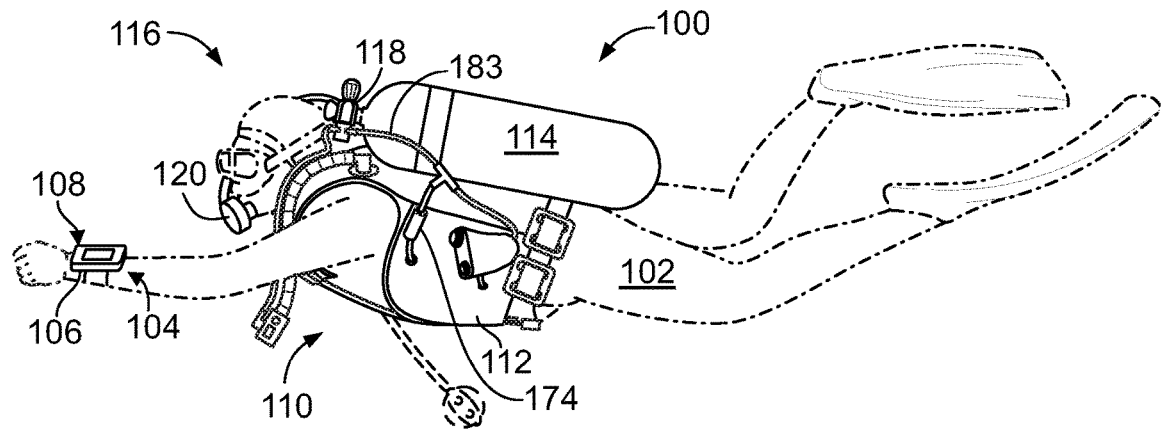
FIG. 1 illustrates a configuration of a safety system, in accordance with an example implementation.
Figure 2:
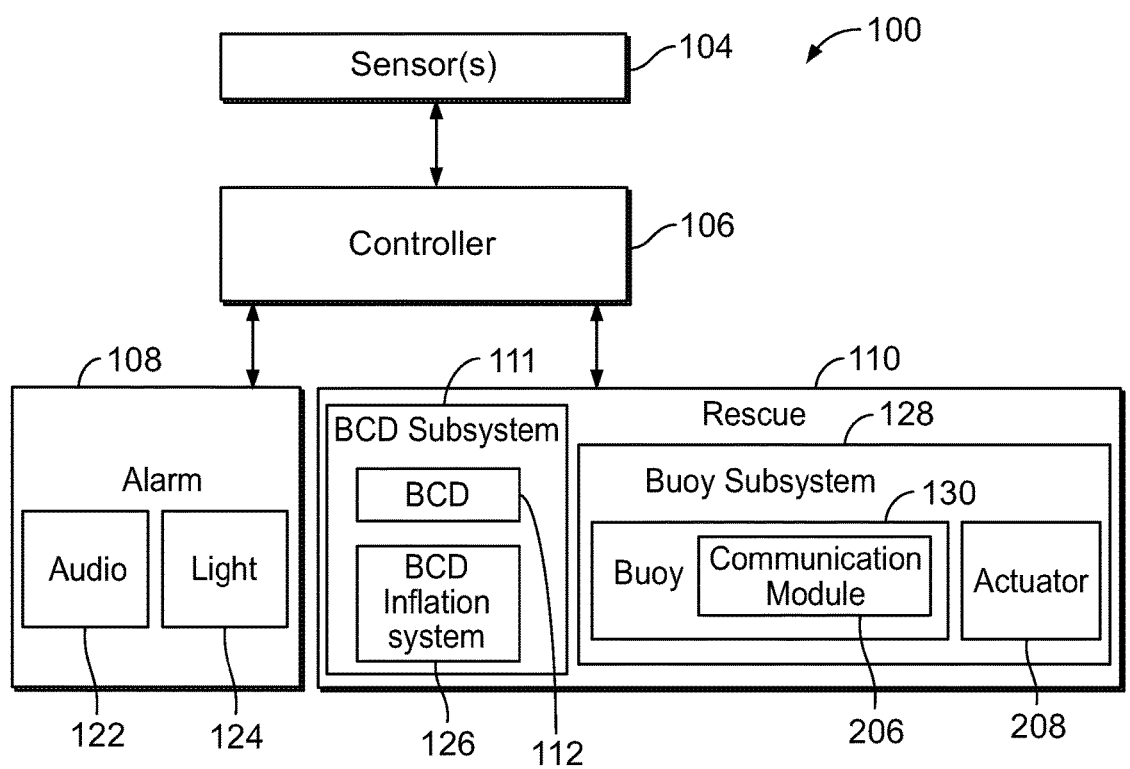
FIG. 2 illustrates an example block diagram of the diving system shown in FIG. 1, in accordance with an example implementation

The appended figures illustrate example embodiments of a safety system 100, including examples of its subsystems. As shown in FIGS. 1 and 2, an underwater diver 102 employing the safety system 100 is wearing one or more sensors 104, a controller 106, an alarm system 108, and a rescue system 110. In the example embodiment shown in FIG. 1, the controller 106 is worn on the body of the diver 102.

The rescue system 110 includes a BCD subsystem 111, which includes a BCD 112 configured to be strapped onto the back of the diver 102 and to hold a tank 114 of compressed gas. A regulator 116 includes a first, or primary, stage atop the tank 114 and a second, or secondary, stage 120 held by diver's mouth.

Detecting and Reporting Pertinent Conditions: Sensors 104

In an example embodiment, the sensors 104 include one or more biological sensors (e.g., sensors or bio-sensors configured to detect the functioning or activity of the diver 102). The controller 106 is in communication with such body-worn, biological sensors. Each such sensor is configured to measure at least one biological parameter of the diver 102 and transmit a biological signal correlated to the biological parameter to the controller 106.

In example embodiments, the sensors 104 measure and report one or more parameters related to the diver's well-being, including, for example, blood oxygen level, blood gas saturation level, pulse rate, blood pressure, respiration rate, and/or other vital signs, and provide data regarding the monitored parameters to the controller 106. Biological sensors are disclosed, for example, in U.S. Pat. No. 9,339,242 ("Systems, methods, components, and software of monitoring and notification of vital sign changes"); U.S. Pat. No. 9,339,237 ("Continuous transdermal monitoring system and method") and U.S. Pat. No. 8,417,351 ("Peripheral oxistimulator apparatus and methods"); U.S. Pat. No. 7,310,549 ("Dive computer with heart rate monitor").

In an example embodiment, the sensors 104 also include equipment sensors. Such sensors help measure, for example, tank gas pressure or the water depth of the diver 102.

One, some, or all of the equipment sensors include a battery power supply and communicate with the controller 106. In example embodiments, communications between the controller 106 and sensors 104 are wired or wireless or a combination of wired and wireless communications.

Examples of various controller embodiments are shown in FIGS. 3-5, 7 and 9. The controller 106 monitors data from sensors 104 regarding salient conditions of the diver's body and/or her equipment and provides information to the diver 102 on a display. The module holding the controller 106 may itself house a variety of sensors, with information from such sensors commonly including for example, the depth of the diver, the time the diver has been submerged and at what depth, and rate of the diver's ascent. An example of a dive computer with wireless communication capabilities is disclosed in U.S. Pat. No. 7,797,124 ("Dive computer with free dive mode and wireless data transmission").

In another example embodiment, optical communications are employed for data transmission. Optical communications may allow a high data communication rate. In other embodiments, acoustic, or audio, transmissions are used additionally or alternatively for communication. Acoustic signals are similar to sonar signals. Acoustic transmissions are generally reliable and travel relatively efficiently in water. The audio signal may or may not be audible to human ears.

In other example embodiments, radio communications are employed for wireless communication between the controller 106 and sensors 104. A radio signal may be a relatively low-frequency electromagnetic signal. A low frequency radio signal typically does not propagate far underwater, but available electronic packages allow transmissions to propagate between, e.g., a diver's pressure gauge and a wrist-mounted dive computer and from one diver to another, nearby diver.

Figure 3:
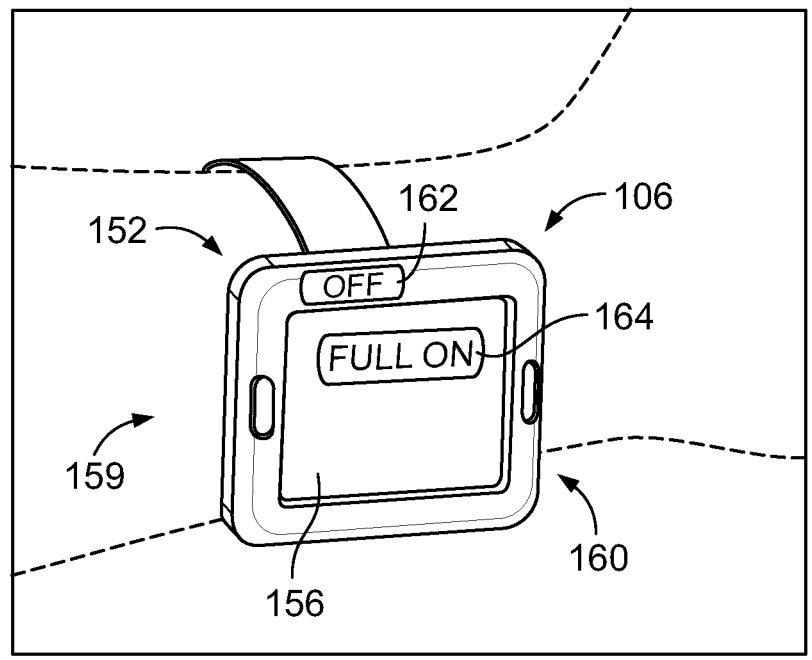
FIG. 3 illustrates an example of a controller, in accordance with an example implementation.

In the example embodiment of FIG. 3, the sensors 104 and controller 106 communicate wirelessly. In the example embodiment of FIG. 4, the sensors 104 and a controller 132 communicate via a wire 134. In another example embodiment, a combination of wire and wireless communications are used. Wireless communications reduce the risk of a diver tangling or breaking a wire. Wired communications can be less expensive to manufacture and can use less battery power to operate. Electrical connections may also be used for power transmission. In some example embodiments, a receiver that another diver has may be able to receive the wireless signal provided by the controller 106. This signal may include data from the diver's body-worn sensors(s), a Caution alarm signal, a Warning alarm signal, and/or a rescue deployment signal.

The controller 106 determines whether a measured parameter value is anomalous (e.g., consistent with a potentially serious condition). If a parameter value is a minor anomaly, the controller 106 issues a Caution alarm signal. If a parameter value is a major anomaly (e.g., consistent with a more serious and time-critical condition), the controller issues a Warning alarm signal. If a parameter value is a critical anomaly (e.g., consistent with an imminent, potentially catastrophic condition), the controller issues an Emergency alarm signal.

The controller 106 communicates with both the alarm system 108 and rescue system 110. In an example embodiment, the alarm system 108 includes an audible alarm 122 and/or a light alarm 124, which activate upon receiving either a Caution or Warning alarm signal from the controller 106.

The rescue system 110 includes a BCD inflation system 126 and a buoy subsystem 128, with the buoy subsystem 128 including a deployable buoy 130. If rescue deployment is enabled in the controller 106 and if a Warning alarm signal is not turned off by the diver 102 or another diver within a time interval after initiation, the controller 106 will issue a rescue deployment signal. The BCD 112 inflates in response to a BCD rescue deployment signal from the controller 106, and the buoy is released in response to a buoy rescue deployment signal from the controller 106.

In example embodiments, biological sensors of the system 100 include a pulse sensor 136, blood oxygen sensor/oximeter 138, and respiration sensor 140, as well as a battery 142. See FIG. 5. In an example embodiment, the sensors 104 also include equipment sensors including a tank gas pressure sensor 144. In example embodiments, the biological sensors include a combined pulse rate detector and oximeter, which is located on the diver's wrist, ear, or fingertip, or elsewhere on the diver. The pulse oximeter 146 is shown on the ear of the diver 102 in FIG. 6. The pulse oximeter 146 reports the level of blood oxygen saturation by measuring relative absorbance of red and infrared light in oxygenated and deoxygenated hemoglobin in the blood. The sensor thus determines the extent to which the diver 102 is undergoing hypoxemia. The pulse oximeter 146 reports pulse rate by analyzing periodic change of the relative absorbance data. Nitrogen gas (or other inert gas) saturation is determined based on reported oxygen saturation and/or on dive profile data including breathing gas composition, depth, and time.

Figure 7:
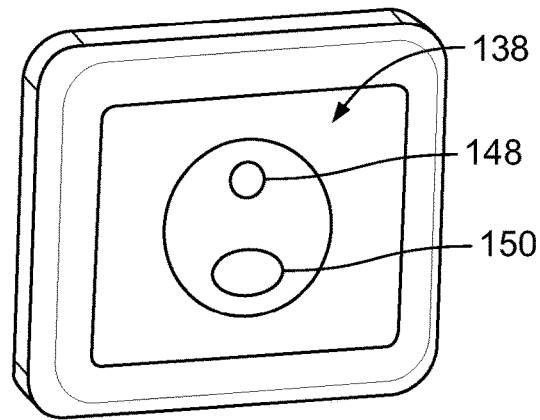
FIG. 7 illustrates an example of sensors on a controller, in accordance with an example implementation.

FIG. 7 shows a side of the controller 106 adjacent the wrist of the diver 102 in FIG. 1. The controller housing includes an oximeter 138 having a source of red light 148 and detector 150 to sense reflection of red light. From such sensor data, the controller 106 determines the blood oxygen content of the diver 102.

Figure 8:
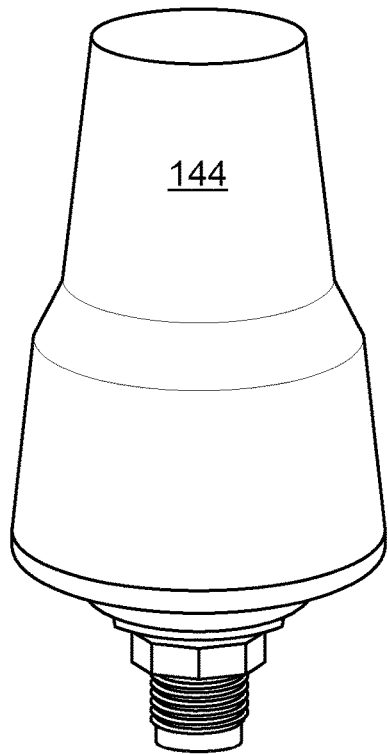
FIG. 8 illustrates an example of a gas pressure sensor, in accordance with an example implementation.

In another example embodiment, the sensors 104 include a heartbeat monitor held adjacent the chest of the diver 102 with chest strap. In an example embodiment shown in FIG. 8, a pressure sensor 144, a type of equipment sensor, detects the pressure of gas in the tank 114. The gas pressure sensor 144 is located at the primary (high pressure) stage 118 of the regulator 116 and reports the pressure of the gas in the tank 114 by generating a wireless equipment signal that is received by the controller 106. An example of a pressure transducer with wireless communication is disclosed in U.S. patent application Ser. No. 14/108,015 ("Pressure valve transmitter with redundant pressure valve indicator").

In an example embodiment, changes in tank pressure over time are also used to determine a real-time respiration rate. The pressure sensor 144 transmits an equipment signal to the controller 106 to report pressure data. It may include a battery power supply to allow wireless operation. A rate of incremental decrease in gas pressure in the tank 114 corresponds to the diver's respiration rate. In another example embodiment, a pressure sensor detects the movement of air in the second stage 120 of the regulator 116, both from the second stage 120 into the diver 102 and from the diver 102 to the exhaust ports of second stage 120, to determine the diver's respiration rate.

A gas composition sensor may determine and report the makeup of the gas being delivered to the diver 102. The sensor is located in the second (delivery) stage 120 of the regulator 116 and engages in wired or wireless communication with the controller 106 (including a wrist module display or other user interface). The sensor in the second stage 120 receives data from the controller 106 and reports to the diver 102 information regarding the acceptable, or toxic, makeup of the gas being supplied to the diver 102.

The system 100 may include other types of sensors to detect parameter values consistent with other serious diver conditions. For example, a parameter value corresponding to stopped heart (i.e., no pulse) or a weak or low-rate heartbeat (i.e., a weak or low pulse) is consistent with a heart attack. A parameter value corresponding to blood with a low-oxygen content is consistent with a diver who with a respiration issue (e.g., drowning or carbon monoxide poisoning). Parameter values consistent with diver at substantial depth that fails to ascend when her tank pressure runs very low is consistent with a diver who is unable to focus mentally (and who may run out of breathable gas (e.g., air) before she can safely return to the surface). It is contemplated that the system 100 can use a wide range of biological and equipment sensors configured to be in communication with the controller 106.

The controller 106 generates an alarm signal upon receiving a signal from a biological and/or equipment sensor that corresponds to a parameter value and determining that the parameter value is anomalous. For example, if the controller 106 receives sensor signals consistent with the diver's respiration rate being too low or the gas pressure in the tank 114 being too low, the controller may then responsively issue signals to initiate Caution alarms, Warning alarms, and/or the deployment of one or both rescue measures.

Receiving Sensor Data: Controller 106

Upon receiving data from one or more sensors 104 (that is, upon receiving a biological signal or equipment signal relating to the value of a particular parameter), the controller 106 determines if the parameter value is anomalous (that is, whether the parameter is outside a range appropriate for the parameter). If a parameter value is anomalous (that is, an anomaly exists), the controller 106 runs a diagnostic test to confirm that that anomaly is not the result of a fault within the system 100. If no fault is detected, the controller 106 moves to an alarm condition.

When in an alarm condition, the controller 106 issues an alarm signal. The controller 106 issues a Caution alarm signal upon detecting a minor parameter value anomaly, a Warning alarm signal upon detecting a major parameter value anomaly, and an Emergency alarm signal upon detecting a critical parameter value anomaly.

In an example embodiment, the controller 106 is configured to compare parameter values derived from the data provided by the sensors 104 to threshold values in a lookup table stored in memory. A parameter value is anomalous if it is either above or below threshold values appropriate for the parameter. The controller 106 has stored in its memory a variety of different threshold values, both for different types of parameters (e.g., pulse rate and respiration rate) and also for different alert levels. The threshold level(s) may be default level(s) programmed in a memory of the controller 106 and/or user-definable threshold level(s).

The determination of whether a parameter value exceeds a threshold (and, thus, whether the controller 106 moves to an Alarm condition) is not limited to an arithmetic comparison of a measured parameter value with a static parameter value in memory. Such a determination may include, for example: an evaluation of other factors such as, for example, the rate of change of a parameter value, how long the anomaly has existed, age of the diver, a comparison of the measured parameter value with a value that is adjusted during a dive to account for the length of the dive, the water depth, the water temperature, etc.

In one example embodiment, the controller 106 issues a Caution alarm signal upon detecting a parameter value above (or below) a first threshold (i.e., outside a first range), where the parameter value is consistent with a less serious (e.g., less dangerous and less time-critical) diver condition. That is, with a minor anomaly in a parameter value, the diver 102 is not at substantial risk if she does not receive prompt assistance. In an example embodiment, a modestly depressed pulse and respiration rate is determined to be minor anomaly and results the controller 106 issuing a Caution alarm signal.

In one example embodiment, the controller issues a Warning alarm signal upon detecting a parameter value above (or below) a second threshold (i.e., outside a second range), where the parameter value is consistent with a more serious (e.g., more dangerous and more time-critical) diver condition. That is, with a major anomaly in a parameter value, the diver 102 is at substantial risk if she does not receive prompt assistance. In an example embodiment, a substantially depressed pulse and respiration rate is determined to be a major anomaly and results in the controller 106 issuing a Warning alarm signal.

In some emergency situations, a diver should rise to the surface of the water and obtain assistance immediately, despite the risk associated with an immediate ascent. In one example embodiment, the controller issues an Emergency alarm signal upon detecting a parameter value above (or below) a third threshold (i.e., outside a third range), where the parameter value is consistent with an extraordinarily serious and time-critical diver condition. That is, with an emergency anomaly in a parameter value, the diver 102 is at imminent risk of a catastrophic result if she does not receive prompt assistance. In an example embodiment, parameter values consistent with the diver breathing in water instead of gas (e.g., air) is determined to be an emergency anomaly and results in the controller 106 issuing an Emergency alarm signal.

Referring to FIGS. 3-5, 9, and 11, the controller 106 communicates with the sensors 104 and also includes a user interface 152 and a battery 154. In various examples, the user interface 152 includes a display 156. The display 156 and a processor within the controller 106 can share the same housing. In the wrist module embodiment shown in FIG. 4, for example, biological data are shown on the display 156, which is an integral part of the controller 106. In another example embodiment, a screen that displays the measurements is physically apart from the housing that encloses the controller processor.

The user or diver-interface 152 also includes user or diver-operable controls 159, including manually operable buttons 160. The buttons 160 may be physical buttons or touch-screen buttons or a combination of both. A physical button (such as the Off button 162) is generally regarded as reliable and intuitive to operate. A touch screen button (such as the Full On button 164 shown in FIG. 3) has fewer moving parts and is easier to configure in different languages, sizes, and colors.

Figure 9:
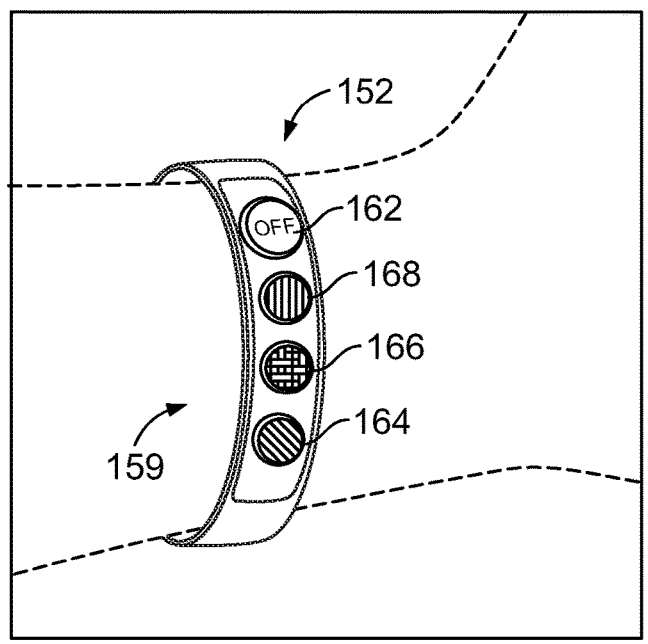
FIG. 9 illustrates an example of a controller using LEDs as a display, in accordance with an example implementation.

In another example embodiment, the controller 106 has no alphanumeric display. Rather, as illustrated in the example of FIG. 9, the user interface 152 has red, yellow and green light emitting diodes (LEDs) 164, 166, and 168 that illuminate to indicate whether parameters measured by the various sensors are within Warning (red), Caution (yellow), or Normal (green) ranges. A simple display made with LEDs may be less expensive to manufacture and also more readily understood by a diver under stress or suffering from nitrogen narcosis.

Figure 10:
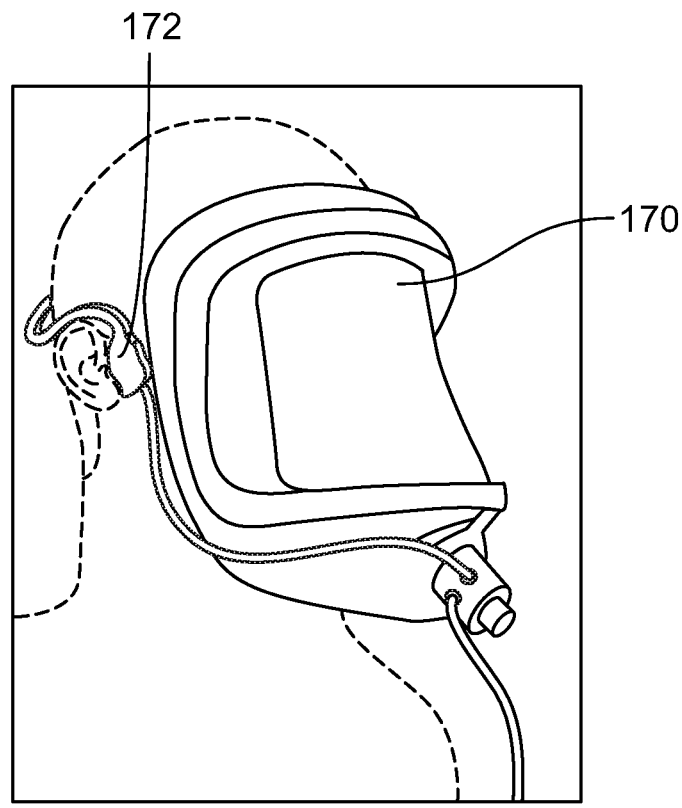
FIG. 10 illustrates an example of diver wearing a full-face mask, in accordance with an example implementation.
Figure 11:
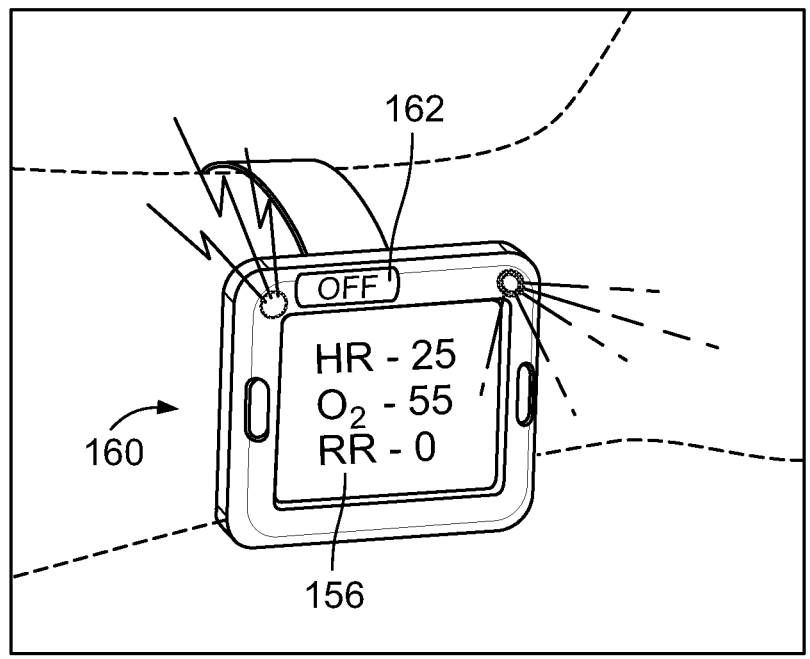
FIG. 11 illustrates an example of an activated alarm, in accordance with an example implementation.
Figure 12:
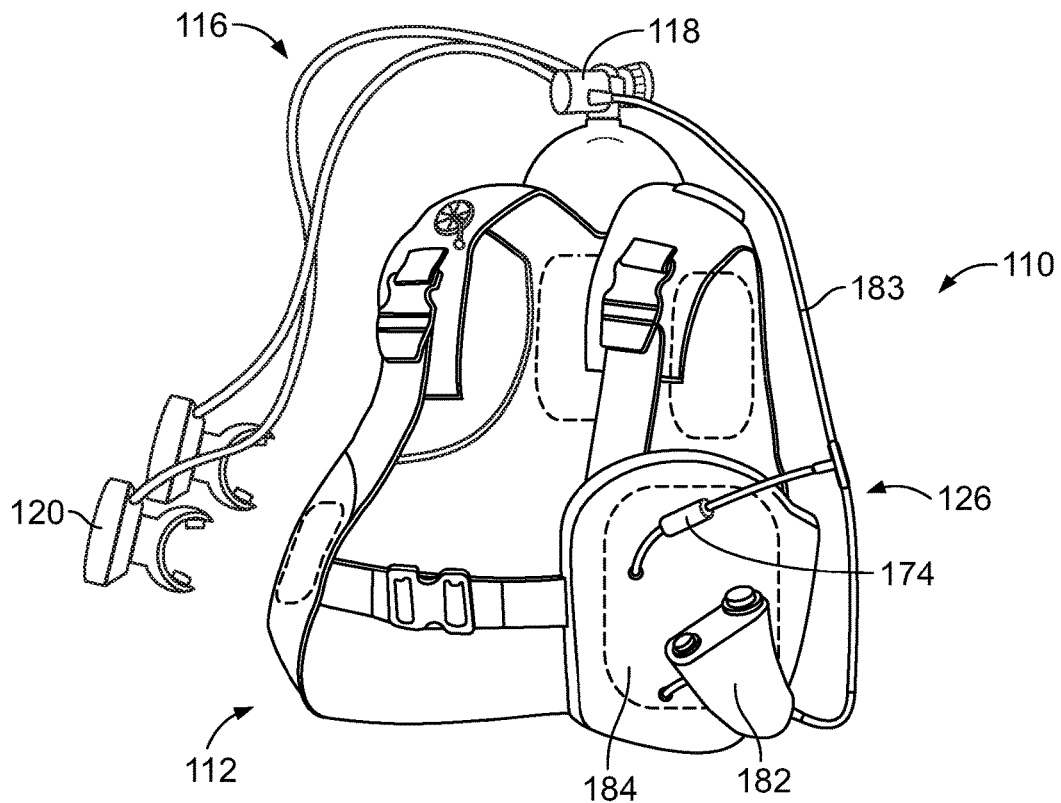
FIG. 12 illustrates an example of a BCD and BCD control valve, in accordance with an example implementation.

Referring to FIG. 10, in another example embodiment, the user interface 152 includes a microphone for accepting audible commands issued by a diver wearing a full-face mask 170. The controller 106 is configured respond to microphone signals as an alternative to, or in addition to, inputs made by pressing buttons. A further, example of a user interface 152 includes a headset for delivering an audio signal to the diver 102. Such an audio signal assists the diver in hearing pertinent information, including any alarm, from the controller 106. The headset may incorporate a bone conduction transducer, headphone, or speaker. In an example embodiment shown in FIG. 10, a bone conduction transducer 172 contacts the diver near her ear and creates sound by conducting vibrations to the diver's skull. An example of a bone conduction transducer is disclosed in U.S. Pat. No. 5,889,730 ("Underwater audio communication system using bone conducted sound").

Issuing Alarms: Alarm System 108

The display 156 provides information to the diver 102 regarding the parameters measured by the sensors 104. The display 156 can provide information regarding parameter values that are within nominally safe ranges (such as in FIG. 4) or parameter values that is anomalous and indicate a serious diver condition (such as in FIG. 11).

Upon receiving sensor data indicating that a diving parameter value is anomalous, the controller 106 conducts a diagnostic test to detect a possible fault condition within the controller 106 or the sensor(s) 104. For example, if the controller 106 detects that a battery voltage is outside an acceptable range or there is an unexpected, internal short (or open) circuit, the controller 106 enters a Fault mode.

Figure 4:
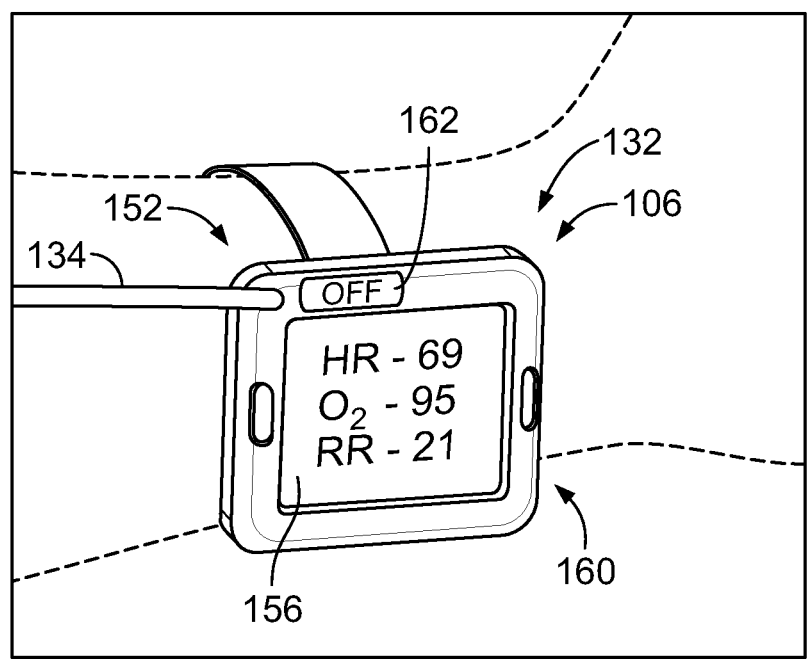
FIG. 4 illustrates another example of a controller, in accordance with an example implementation.

In the Fault mode, the controller 106 indicates that a fault has been detected, for example, by flashing the word, "Fault," on the display 156 shown in FIG. 4, or by flashing simultaneously all of the LEDs 164, 166, 168 shown FIG. 9. This indicates the system 100 cannot be relied upon. In an example embodiment, the system 100 deploys no rescue measures when in Fault mode.

Upon sensing an anomaly (i.e., upon detecting a parameter value outside an acceptable range), the controller 106 assumes an alarm condition and issues an alarm signal. An alarm condition may be triggered, for example, by: an oxygen saturation level below a threshold value (e.g., below 90% saturation); a respiration level below a threshold value (e.g., below 6 breaths per minute); and/or an unsafe pulse rate (e.g. (a) less than 30 beats per minutes, or (b) more than 230 beats per minute minus the age of the diver).

In another example embodiment, the controller 106 assumes an alarm condition and thus issues an alarm signal if, for example, a diver breathing air at 40 meters or more of depth needs to begin ascending if she is to have enough air for a safe ascent; however, instead of ascending, she swims deeper. Such behavior may indicate the diver has become disoriented and needs help. In another example embodiment, an alarm condition exists if a diver descends below a predetermined depth.

In an example embodiment, the controller 106 issues a Caution alarm signal upon sensing a minor parameter value anomaly. The Caution alarm signal causes the display 156 to show a yellow "Caution" screen, and/or sound a low-pitch, audible Caution alarm (e.g., buzzer), and/or slowly flash a light (e.g., LED or strobe light). The controller 106 issues a Warning alarm signal upon sensing a major parameter value anomaly. The Warning alarm signal causes the display 156 to show a red "Warning" screen, and/or sound a high-pitch, audible Warning alarm, and/or quickly flash a light.

In one embodiment, the controller 106 in an alarm condition causes audio and/or visual alarms to pulse on and off at rates between 0.5 and 5 hertz. Such an intermittent alarm signal saves energy in the system battery(ies), by allowing reduced duty cycle. The intermittent alarm also makes the alarm(s) easier for divers to discern over any generally constant background noises or light.

In another example embodiment, the controller 106 also includes a vibration motor, which is activated upon the controller 106 entering the alarm condition. The vibration motor vibrates at different speeds in response to either a Caution alarm signal or Warning alarm signal. Such an arrangement helps to alert a distracted diver to a potentially adverse condition indicated by an anomalous parameter value.

The controller 106 may also issue a limited-range radio-wave alarm signal and/or activate light and/or acoustic alarms for other divers in the area. In an example embodiment, an alarm signal is received by a controller worn by another diver in the vicinity (e.g., a "diving buddy"), alerting her that a nearby diver may need assistance. A flashing light or pulsing audio alarm worn by a stricken diver 102 (activated by the alarm signal from the controller 106) may similarly alert a nearby diver. If the alarm is detected by a nearby diver, she can assess the condition of the diver 102 whose controller initiated the alarms and take any required, remedial action. The diver or diving buddy may activate a diver-operable stop input, such as the Off button 162, to deactivate the alarm(s) and/or prevent the deployment of one or both rescue measures.

After activation, the controller 106 continues to stay in the alarm condition as long as the alarm has not been manually deactivated with the diver-operable stop input (e.g., Off button 162) and the parameter value or values that triggered the alarm condition remain anomalous (i.e., the condition that triggered the alarm condition is persists). If the controller 106 is in a Caution alarm condition (and not the more serious, Warning alarm condition), the alarm stays activated (e.g., the audible alarm and/or light stay on), but the system 100 does not deploy any rescue measures unless the controller 106 detects a major anomaly in a parameter value (or receives a manual input instructing the controller 106 to deploy one or both rescue measures).

If the controller 106 persists in the Warning alarm condition for a time interval, and one or more parameter values remains a major anomaly (i.e., time critical and posing substantial risk to the diver 102), and the diver-operable stop input (e.g., the Off button 162) has not activated, then the system 100 deploys one or more rescue measures. In one example embodiment, the time interval is a predetermine period of time, such 5 to 15 seconds. In another example embodiment, the time interval is determined based upon the severity of the major anomaly. (In an example embodiment, the time interval for an Emergency alarm condition is zero to five seconds.) Upon the expiration of the time interval (if any), the controller 106 issues a rescue deployment signal. In an example embodiment, the rescue deployment signal may include an ascent control signal and/or a buoy release signal and/or a weight release signal.

Rescue Measures Generally

Referring in particular to the example embodiments shown in FIGS. 1, 2, 5, 12, 21, the rescue system 110 includes the BCD subsystem 111 and buoy subsystem 128. The example BCD subsystem 111 includes the BCD 112 and a BCD inflation system 126. The BCD inflation system 126 includes a BCD value 174, BCD actuator 176, and battery 178. The buoy subsystem 128 includes the deployable buoy 130. The BCD 112 is inflated and/or the deployable buoy 130 is released upon the controller 106 issuing a rescue deployment signal.

In an example embodiment, the controller 106 has (excluding the Fault mode) seven primary modes of operation, as described below.

Off. When in the Off mode, the system 100 activates no alarm, nor does it deploy any rescue measure, unless and until it receives an input to change to a different mode. In an example embodiment, the user interface 146 includes the "Off" button 162. When pushed by, for example, the diver 102 or a nearby diver, the alarm signal is turned off and the rescue subsystem 110 remains off until activated again with the user interface 152.

Full On (also referred to as Open Water mode). The controller 106 generally issues alarms and rescue deployment signals, as described below. See FIG. 3.

Alarm Only (also referred to as Cave or Wreck Diving mode). The controller 106 issues Caution or Warning alarm signals, as appropriate, upon detecting an anomaly; however, the system 100 does not deploy any rescue measure (BCD inflation or buoy release).

Caution Alarm Off. The controller 106 does not issue any Caution alarm signal (which may be preferred by a diver when she is aware of a minor anomaly and does not want the distraction of a visual or audio Caution alarm). The controller 106 will still issue a Warning alarm signal and deploy rescue measures upon detecting a major anomaly.

All Alarms Off. The controller 106 does not issue any alarm signal. The system 100 will still deploy rescue measures upon detecting a major anomaly in a parameter value.

Diver-Elected Ascent. The diver 102 may activate the user interface 152 to inflate the BCD 112, regardless of whether or not an anomaly has been detected or an alarm signal has issued. The rescue system 110 will bring the diver 102 to the water surface at a controlled rate (or, if the diver 102 so instructs the controller 106 via the user interface 152, at an unconstrained, emergency ascent rate).

Diver-Elected Buoy Release. The diver 102 may activate the user interface 152 to release the buoy 130, regardless of whether or not any anomaly has been detected or any alarm signal has issued.

When the controller 106 receives data from a sensor 104 indicating a major anomaly in a parameter value, the controller 106 determines its current mode of operation. If in an appropriate mode, the diagnostic check conducted by the controller 106 and/or sensors 104. If no fault is detected and (assuming a non-emergency alarm condition) the major anomaly persists for an interval of time following the initiation of a Warning alarm signal, the controller 106 sends a rescue deployment signal, either via a wire or wirelessly. The deployment signal results in a gas being sent to a balloon or other bladder, to help the diver ascend to the surface, and/or a buoy being released. In example embodiments, the deployment signal is received by the BCD valve 174 and/or BCD actuator 176.

In the example embodiment shown in FIG. 1, the controller 106 is on the wrist of the diver 102, physically separate from either the BCD 112 or buoy 130. Accordingly, the diver 102 need only maintain and work with one (e.g., wrist-mounted) computing module and user interface, rather than separate computing modules on the BCD 112 or buoy 130. With such an example embodiment, the diver 102 needs to check the battery charge level for only one computer module, rather than multiple computer modules, before a dive. Particularly in stressful circumstances, a diver having to contend with only one dive computer and interface (rather than multiple computers and interfaces) can reduce the chance of diver error and, thus, reduce the risk of an adverse outcome.

Sonar Component 180

Figure 13A:
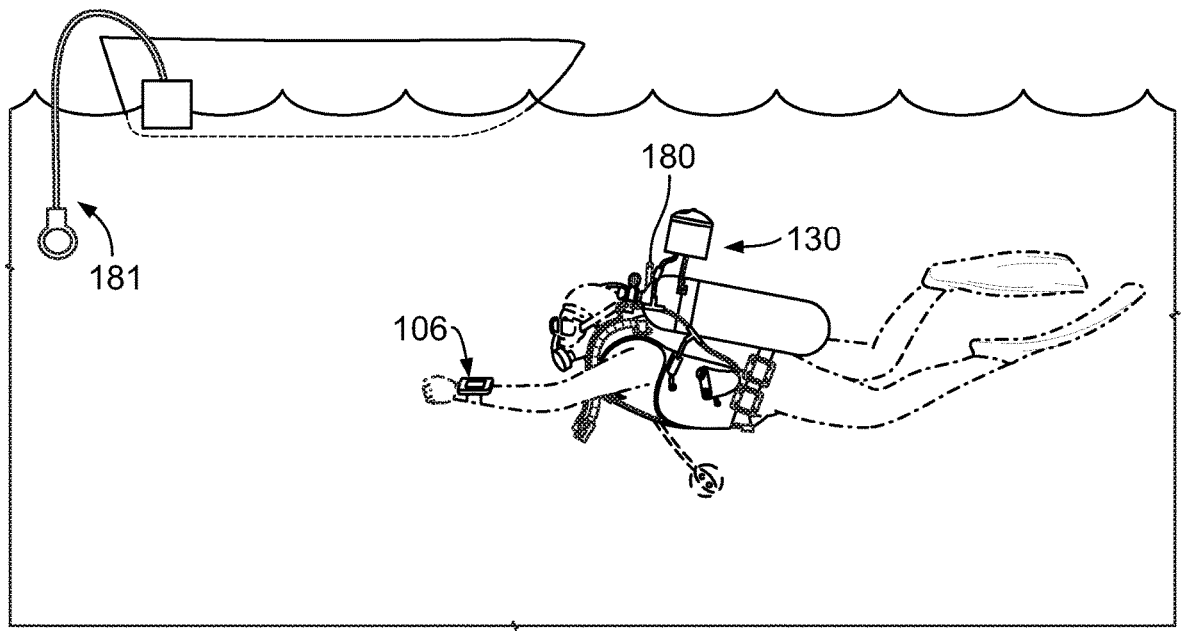
FIG. 13A illustrates an example of a diver carrying a buoy, along with personal sonar system, in accordance with an example implementation.

Referring to FIG. 13A, an example embodiment of the system 100 also includes a personal sonar component 180 to detect nearby obstructions, such as a cave or wreck ceiling. An example of a sonar system is disclosed in U.S. Pat. No. 7,272,075 ("Personal sonar system"). If the sonar component 180 detects an obstruction above the diver, the controller 106 switches to "Cave/Wreck" modes, resulting in the rescue subsystem 110 being disabled until the sonar component 180 no longer detects an obstacle above the diver 102.

In some instances, the diver 102 initiates a dive from a dive boat. After spending time underwater, she wishes to return to the boat, but does not know the location or the boat relative to her position. She then typically swims to the surface and attempts to locate the boat visually. If she wishes to continue diving, she determines a compass heading for the boat and then, upon continuing her underwater dive, attempts to follow the compass heading she determined at the surface.

In another example embodiment, the boat includes a signal generator, power amplifier, and electro-acoustic transmitter/transducer 181 configured to transmit pulses of sound ("pings"). In various, example embodiments, a serious of pings are transmitted on an ongoing basis, either at regular time intervals or in response to receiving a ping sent by the sonar component 180 on the diver 102.

Figure 13B:
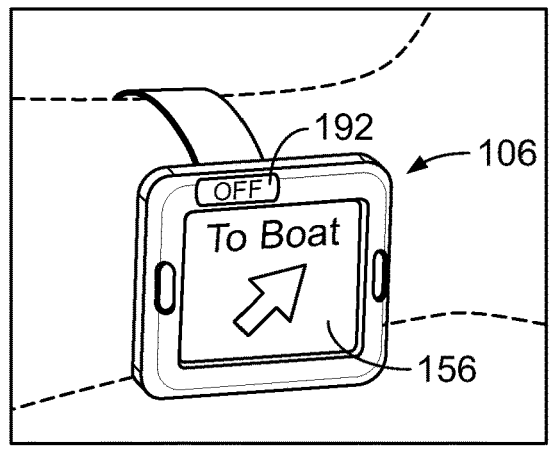
FIG. 13B illustrates an example of a controller, in communication a sonar system, displaying the direction of a dive boat, in accordance with an example implementation.

In an example embodiment, the personal sonar component 180 carried by the diver 102 has an array of sensors oriented in different directions, each of which detects pings. A comparator within the sonar component 180 determines which sensor(s) in the array received the highest energy ping and, accordingly, infers the direction from which the pings emanated. The sonar component 180 then relays such information to the controller 106, which indicates, on the display 156, the direction the diver 102 should swim if she wishes to return to the boat. In the example embodiment of FIG. 13B, the display 156 shows an arrow pointing toward the boat. In another example embodiment, the display 156 identifies the compass heading the diver 102 should follow to reach the boat.

BCD Inflation Generally

Typically, the BCD 114 allows the diver 102 manually to operate a valve 182 manually and divert gas from the tank 112, via a supply hose 183 connected to the first stage 118 of the regulator 116), into one or more bladders 184 within the BCD 112. See FIGS. 12, 14 and 15. In some instances, a dedicated tank is used for BCD inflation, but this is less common.

Moving gas from the tank 114 to the bladder 184 of the BCD 114 (generally at a lower pressure than the gas is stored in the tank 112) results in the combination of the tank 114, diver 102, and BCD 112, as a whole, having an increased volume, but the same mass. As such, the combination as a whole is less dense and more buoyant.

In an example embodiment, the BCD valve 174 of the system 100 is a waterproof, electrically operated, normally-closed solenoid valve. A power supply (e.g., the battery 178) provides power to the BCD valve 174, which includes an actuator, or solenoid 186, to move an internal member 188 within the valve body 190. In the example embodiment shown in FIG. 14, the internal member 188 is an axially moveable spool. In another, alternative example embodiment, the actuator of the BCD valve 174 is a stepper motor, rather than a solenoid, to move the internal member 188 between the positions shown in FIG. 14.

According to an example embodiment, applying electrical power to the solenoid 186 opens the BCD valve 174, and removing power closes the BCD valve 174. The power supply (e.g., the battery 178) may be located at the BCD valve 174 and operate in response a wirelessly transmitted signal from the controller 106. In an alternative, example embodiment, a power conduit electrically connects the BCD valve 174 to a remote power supply. The BCD valve 174 may be located at the first stage (on an intermediate or low-pressure port). In an alternative example embodiment shown in FIG. 12, the BCD valve 174 is downstream, on the low-pressure supply hose 183.

Figure 14A:
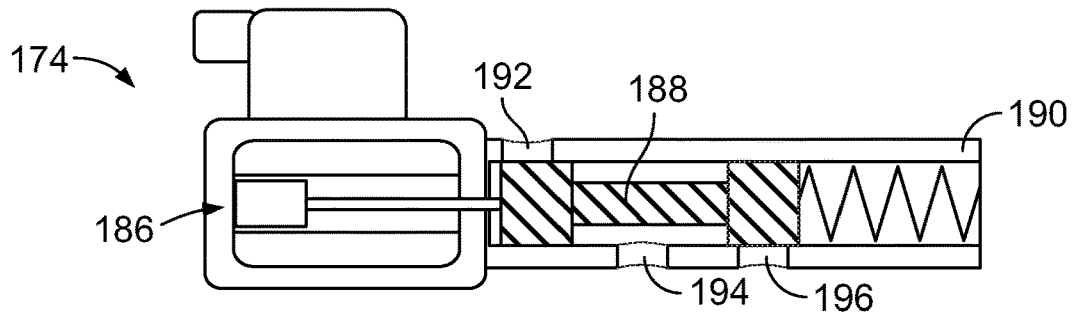
FIG. 14A illustrates a cross-sectional view of an example of a BCD control valve in a position that blocks supply air from both the BCD port and vent port, in accordance with an example implementation.
Figure 14B:
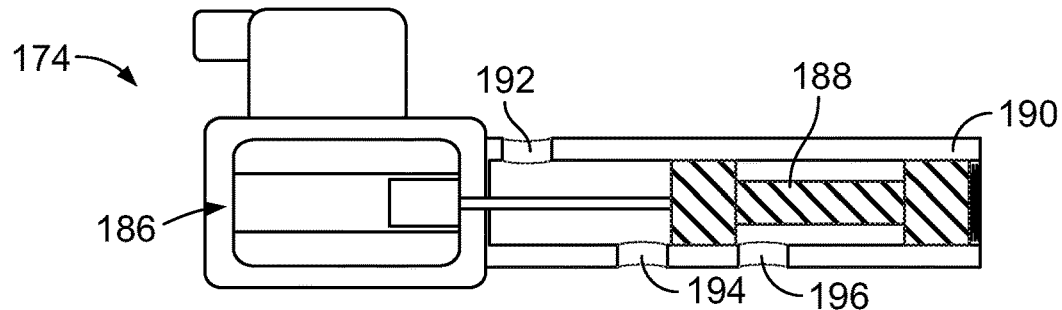
FIG. 14B illustrates a cross-sectional view of an example of a BCD control valve in a position that allows supply air to flow to the BCD port but not to the vent port, in accordance with an example implementation.

Upon receiving a rescue deployment signal from the controller 106, the solenoid 186 of the BCD valve 174 moves the internal member 188 from the position shown in FIG. 14A (where pressurized gas from the supply hose 183 is blocked) to the position shown in FIG. 14B (where pressurized gas flows from the supply hose 183 into the bladder 184 of the BCD 112. When the controller 106 determines that the gas in the bladder 184 should be vented to the environment, the solenoid 186 moves the internal member 188 to the position shown in FIG. 14C.

Controlled Ascent

A depth sensor associated with the controller 106 senses the ambient water pressure over time, allowing the controller 106 to monitor its ascent rate. The depth sensor may be located in the wrist module portion of the controller 106 or elsewhere. An example of a dive computer configured to determine ascent rate is disclosed in U.S. Pat. No. 5,156,055 ("Ascent rate meter for scuba divers").

Upon determining that the rescue measure of BCD inflation should be deployed, the controller 106 issues a rescue deployment signal. In an example embodiment, one type of rescue deployment signal is an ascent control signal. The ascent control signal controls the operation of the BCD valve 174, instructing it to move the internal member 188 with the valve body 190 to the positions shown in FIG. 14.

Absent a time-critical emergency, the gas volume in the BCD 112 is controlled (i.e., gas is added to, or allowed to escape from, the BCD 112) to keep the ascent speed at a safe speed, such as, for example, 30 feet per second. Absent an emergency condition, where the controller 106 determines the diver 102 should be brought to the surface immediately, the controller 106 determines when the diver 102 is ascending too quickly (e.g., faster than approximately 30 feet per minute), too slowly (e.g., substantially slower than approximately 25 feet per minute) or is the ascent rate is within a safe range (e.g., approximately 25 to 30 feet per second).

At one or more points during her ascent, it may be appropriate for the diver 102 to stay at a particular depth in the water (e.g., 15 feet) for a "safety" or "decompression" stop, as a precaution against the bends. In one example embodiment, the controller 106 determines whether one or more safety stops are required and, if so, regulates the BCD valve 184 accordingly. For such a stop, the controller 106 regulates the BCD valve 184 such that the diver 102 ascends at 30 feet per second, slows and then stops ascending at an appropriate depth (e.g., 15 feet) and stays that this depth for an appropriate time (e.g., three minutes). Thereafter, with the stop completed, the controller 106 again provides an ascent control signal to the BCD valve 174 to allow more gas into the BCD 112 and allow the diver 102 to continue her ascent (either to the water surface or to another decompression stop).

As generally shown in FIG. 14, the BCD valve 174 has, within the valve body 190, an inlet port 192, outlet port 194, and the vent port 196. The internal member 188 is configured to move between first, second, and third positions. In the first position, the internal member 188 blocks the inlet port 192 (so gas from the tank 114 does not enter the BCD 112). In the second position, the internal member 188 defines a passageway between the inlet and outlet ports 192, 194, such that pressurized gas from the tank 114 flows through the inlet port 192, through the passageway, through the outlet port 194, and into the bladder 184 of the BCD 112. In the third position, the internal member 188 blocks the inlet port 194 and defines a passageway between the outlet and vent ports 194, 196, such that gas in the bladder 184 flows though the outlet port 194, through the passageway, through the vent port 196, and into the environment (e.g., the water surrounding the diver 102). Because the volume of gas in the bladder 184 generally expands as water depth decreases, it may be necessary, as the diver 102 ascends, to bleed gas from the BCD 112 via the vent port 196.

The solenoid 186 receives the rescue deployment signal provided by the controller 106. The rescue deployment signal includes an ascent control signal and, in response to the signal, the solenoid 186 responsively moves the internal member 188 to the second position when the rate of ascent is below a minimum threshold, moves the internal member 188 to the third position when the rate of ascent is above a maximum threshold, and moves the internal member 188 to the first position when the rate of ascent is within the minimum and maximum thresholds. In one example embodiment, the internal member 188 moves to the second position (adding gas to the BCD 112) when the ascent rate is substantially below 30 feet per minute, moves to the first position (blocking the inlet and outlet ports 192, 194) when the ascent rate is approximately between 25 and 30 feet per minutes, and moves to the third position (allowing gas to vent from the BCD 112) when the ascent rate is substantially above 30 feet per minute.

Figure 14C:
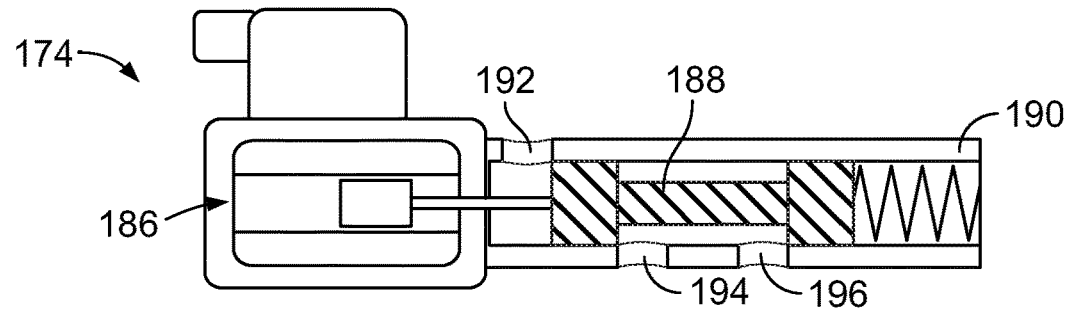
FIG. 14C illustrates a cross-sectional view of an example of a BCD control valve in a position that allows air to flow from the BCD port to the vent port, in accordance with an example implementation.
Figure 15:
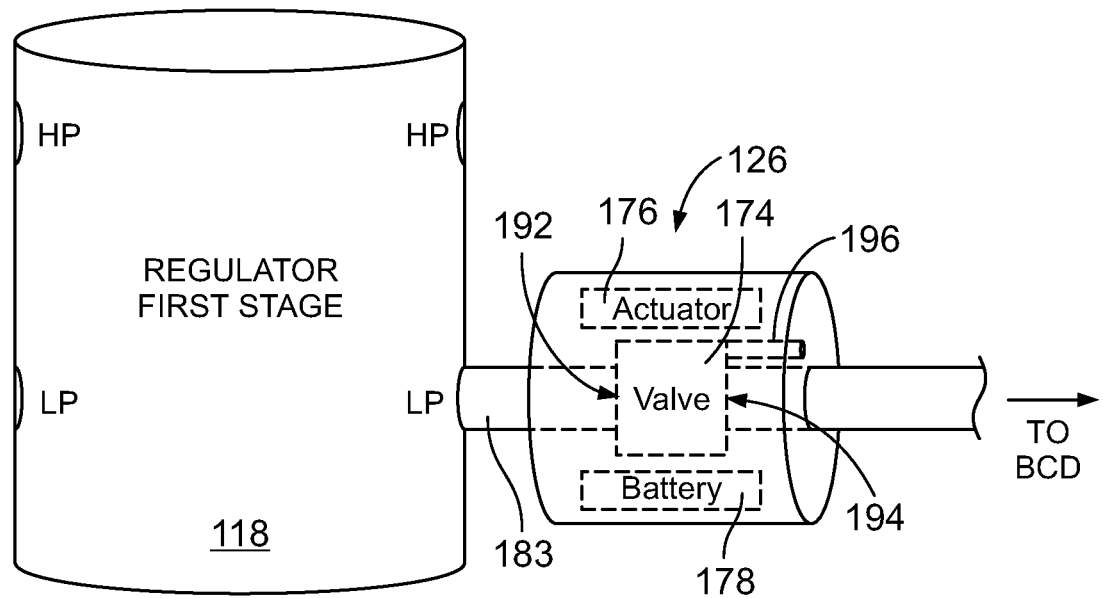
FIG. 15 illustrates an example of a diagram of a BCD control valve in communication with the low pressure port of the first stage of a regulator, in accordance with an example implementation.

In an example embodiment, the BCD valve 174 that supplies gas to the BCD 112 is a three-way solenoid valve that allows a closed connection (FIG. 14A), an open, regulator-to-BCD connection (FIG. 14B), and an open, BCD-to-environment connection FIG. 14C). In one particular example embodiment, to supply gas to the BCD bladder 184, the BCD valve 174 is connected with a DC power supply in normal polarity to actuate the solenoid 186 and move the BCD valve 174 to the open, regulator-to-BCD position. See FIG. 14B. To vent, or bleed, gas from the BCD 112, the solenoid 186 may be connected with the DC power supply source in reversed polarity to actuate the solenoid 186 and move the BCD valve 174 to the open BCD-to-environment position, where it can release gas from the BCD 112 via, e.g., the vent, or bleed, port 196. See FIG. 14C. The solenoid 186 may include a three-way switch, or multiple switches, to move between the normal-off-reversed polarity conditions.

Even if no anomaly exists, the diver 102 may activate the user interface 152 of the controller 106 to activate the BCD valve 174. This will cause a controlled flow of gas from the tank 114 into and, as necessary, out of, the BCD bladder 184 for a controlled assent to the surface. Such an event may occur not because of sensor data indicating an anomalous parameter value, but only because the diver 102 wishes the system 100 to control her ascent, including her safety, or decompression, stops.

Thus, the controller 106 may determine a dive profile for the diver 102; determining when she should surface, as well as how many decompression stops are indicated, at what depths, and for how long. The ascent control signal provided by the controller 106 to the BCD valve 174 adjusts the position of the internal member 188 so that the diver 102 generally follows the dive profile, including depression stops. The preferred rate of ascent during a decompression stop is typically zero (rather than, for example, 30 to 60 feet per second). Thus, in an example scenario, for a diver at 100 feet, the controller 106 may instruct the BCD valve 174 to inflate, and deflate, the BCD 112 to achieve an ascent rate of approximately 30 feet per minute until the diver 102 approaches 15 feet. Then, the controller 106 adjusts the rate of ascent so that the diver 102 stays at 15 feet of depth for three minutes (for a typical safety, or decompression, stop) and the again instructs the BCD valve 174 to allow additional gas into the BCD 112 and cause the diver 102 to ascend safely the remaining 15 feet.

Unconstrained Ascent

As indicated above, in some emergency situations (e.g., where the anomalous parameter value(s) are extraordinarily serious), a diver should rise to the surface immediately. In such a case, upon the controller 106 issuing the Emergency alarm signal, the assent rate limit is bypassed, and the diver 102 is brought to the surface at a faster speed.

Upon receiving the Emergency alarm signal from the controller 106, the solenoid 186 moves the internal member 188 to the position shown in FIG. 14B. That is, the BCD valve 174 is left in the open, regulator-to-BCD position for an emergency, unconstrained ascent. Most modern BCDs contain over-pressure safety bleed valves, which mitigate the risk of over-pressurizing the BCD 112.

In an example embodiment, the diver 102 also has the option to employ the user or diver interface 152 to enter an unambiguous instruction for an unconstrained ascent. If the controller 106 has been configured to accept such an instruction, it will send an emergency, unconstrained ascent control signal to the BCD valve 174, keeping the BCD valve 174 in the open position at least until the diver 102 reaches the water surface.

Weight Belt Ditching

Figure 16:
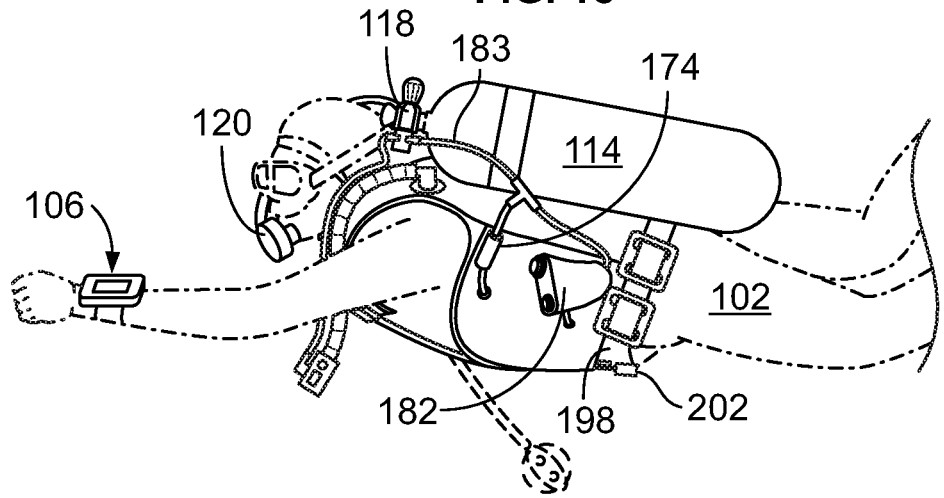
FIG. 16 illustrates an example of a diver wearing a weight belt with a releasable buckle, in accordance with an example implementation.
Figure 17:
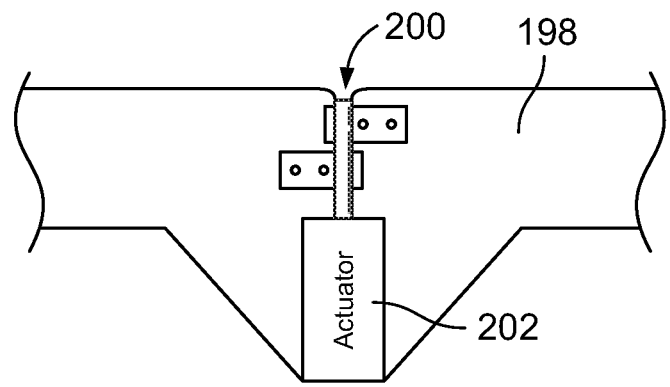
FIG. 17 illustrates an example of the releasable buckle shown in FIG. 16, in accordance with an example implementation.
Figure 18:
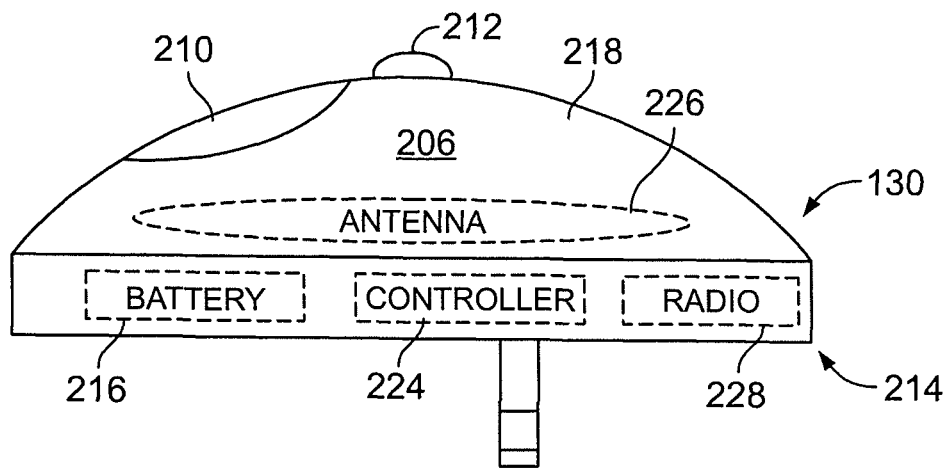
FIG. 18 illustrates an example of a naturally supernatant buoy, in accordance with an example implementation.

Particularly if a diver is wearing a wet suit or dry suit, she may also wear a weight belt, so as to help her more easily achieve a desired buoyancy during a dive. To further assist the ascent of a diver in an emergency (e.g., when the, the controller 106 detects a persistent, major anomaly), another example embodiment also includes a weight belt 198, buckle 200, and buckle actuator 202, as shown in FIGS. 16-17.

In addition to sending a BCD rescue deployment signal to the BCD actuator 176 to inflate the BCD 112 of a stricken diver, the controller 106 (in some but not all embodiments) also sends a weight release rescue deployment signal (another type of rescue deployment signal) to the buckle actuator 202 associated with the diver's weight belt buckle 200. Upon receiving the signal, the buckle actuator 202 disengages the ends of the weight belt 198, allowing the weight belt 198 to fall away from the diver 102.

Personal Buoy for Emergency Notification

Buoy Subsystem 128

The system 100 may be configured to enable communication with others. In some example embodiments, the communication is one-way. If the system 100 senses an anomaly in a biological and/or equipment parameter value, the system 100 provides an alarm to the distressed diver and/or other divers and/or other people at the surface. In one example embodiment, an alarm signal actuates a flashing light and audio speaker, as well as advising a controller worn by a nearby diver that an anomalous parameter value has been detected. Under some environmental conditions, the light and audible alarms can be detected by other divers, and the light alarm can be seen by others on the surface. In another example embodiment, one type of alarm issues for a minor anomaly (e.g., a slower-flashing light and a lower-pitched audible alarm) and another type of alarm issues for a major anomaly (e.g., a faster-flashing light and a higher-pitched audible alarm).

Figure 5:
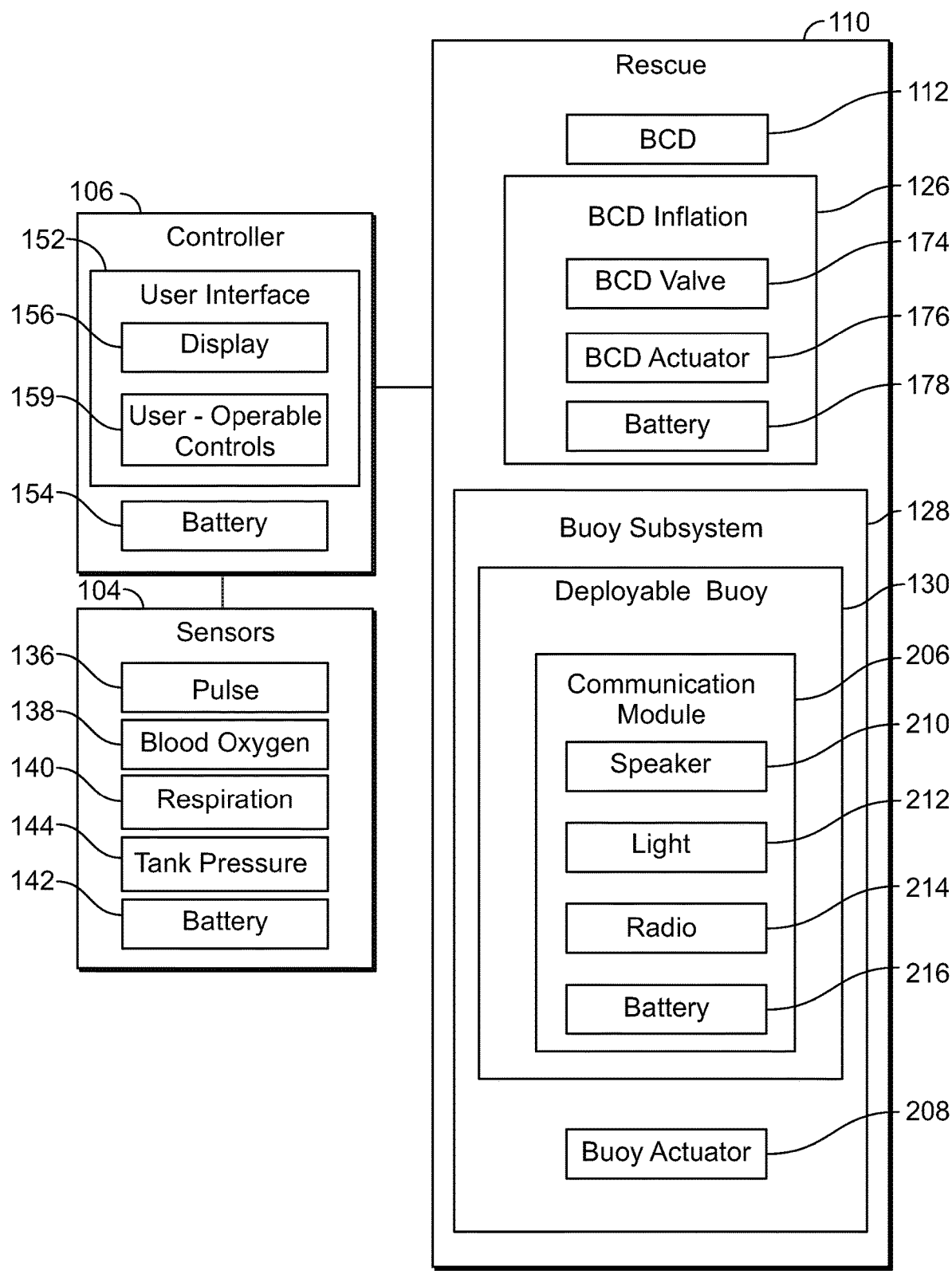
FIG. 5 illustrates an example of block diagram of sensors, a controller, and a rescue subsystem, in accordance with an example implementation.
Figure 6:
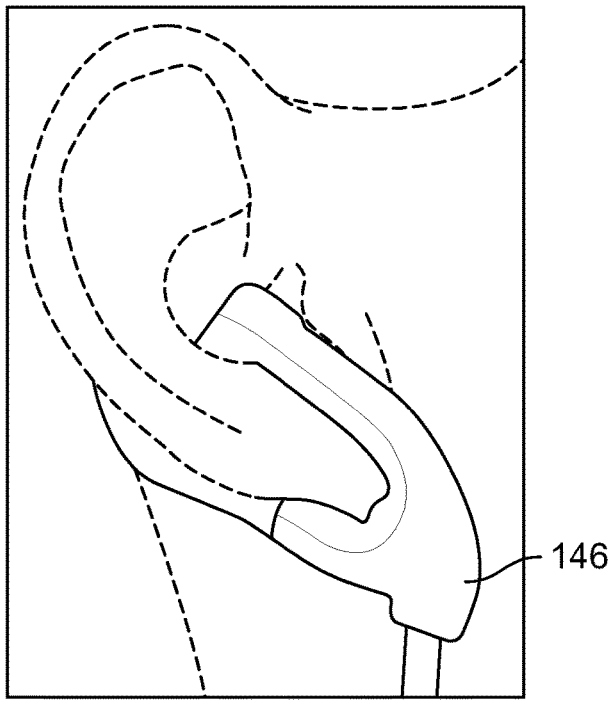
FIG. 6 illustrates an example of oximeter, in accordance with an example implementation.

Referring to FIG. 5, in other example embodiments, the system 100 also communicates to others with the buoy subsystem 128. The buoy subsystem 128 includes the deployable buoy 130, which has a communication module 206, and a buoy actuator 208. The communication module 206 includes a speaker assembly 210, one or more lights 212, a radio module 214, and a battery 216.

Figure 21:
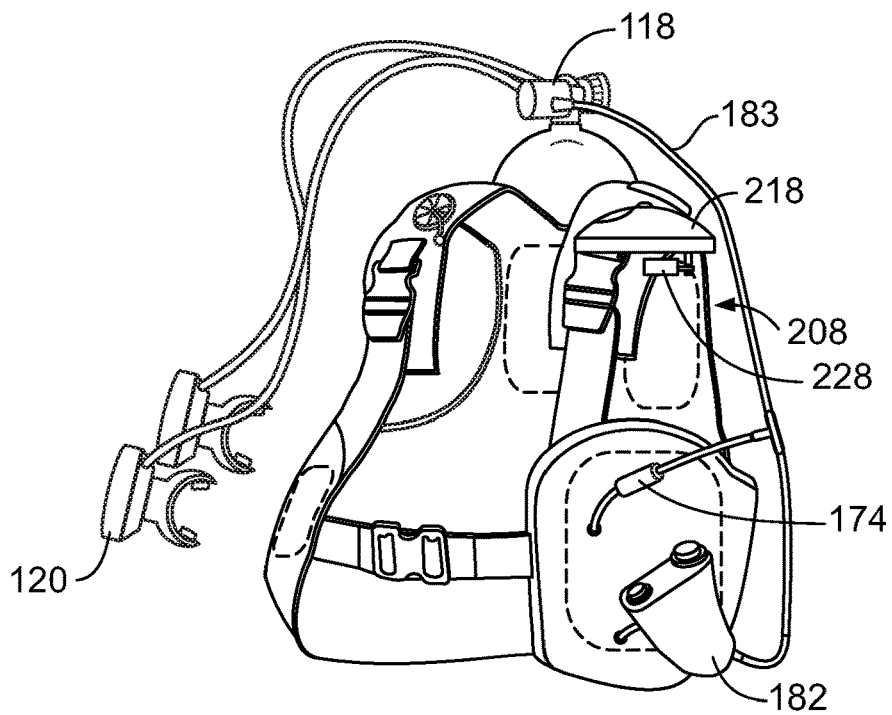
FIG. 21 illustrates an example of a BCD and naturally supernatant buoy, in accordance with an example implementation
Figure 25:
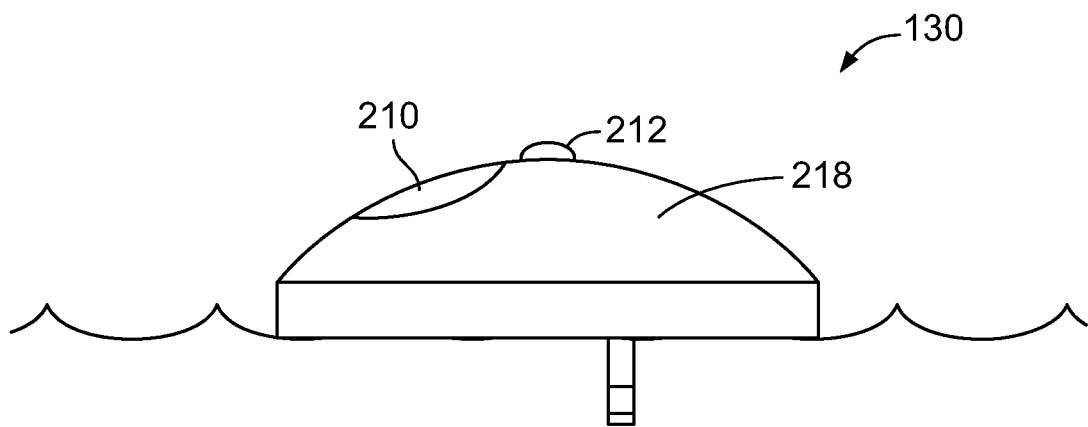
FIG. 25 illustrates an example of a floating, naturally supernatant buoy, in accordance with an example implementation.

In one example embodiment, the buoy 130 is a naturally supernatant (i.e., naturally buoyant), such as the buoy 218 shown in FIGS. 21 and 25. In another example, the buoy 130 is inflatable, such as the buoy 220 shown in FIGS. 19 and 26. The buoy 130 ascends toward the water surface when released. An inflatable buoy 220 is less bulky for a diver 102 to carry. A naturally supernatant buoy 218 does not require an inflation mechanism and, with a larger floatation balloon, is capable of lifting a heavier load in the water.

If the controller 106 is in an appropriate mode of operation and issues a rescue deployment signal, the buoy actuator 208 releases the buoy 130, allowing it to ascend. Once on the surface, the speaker assembly 210 and light 212 alert others on the surface. The audio and light alarms may signify that an underwater diver in the vicinity of the buoy 130 may require attention.

For example, upon breaking the surface, they buoy 130 may alert a rescue diver on the surface, allowing her to reach more quickly the approximate location of a stricken diver. By moving toward the location of the buoy before the stricken diver arrives at the surface, the time delay in reaching the stricken diver may be reduced.

The radio module 214 is configured to transmit and/or receive radio waves. The radio module 214 includes a buoy controller 224, antenna 226, and radio (transmitter and/or transceiver) 228. After being released from the diver 102, the radio 228 broadcasts a "Mayday," SOS, or other signal, via the antenna 226, to indicate distress. In another example embodiment, the buoy controller 224 includes a GPS receiver, in communication with the radio transmitter, for determining the GPS coordinates of the buoy 214. The radio 228 then broadcasts the GPS coordinates as part of the distress signal.

In another example embodiment, the diver 102 may wish to alert, or otherwise communicate with, others at the surface, while remaining submerged. For example, a diver may wish to stay with another injured diver, while still summoning help. In this case, the diver 102 may activate the user interface 152 of the controller 106 to deploy the buoy 130, even when the system 100 has detected no anomaly associated with the diver 102 wearing the system 100.

During at least the initial portion of a dive, the buoy 130 is coupled to the buoy release mechanism or actuator 208. Upon receiving a rescue deployment signal from the controller 106, the buoy actuator 208 may, according to example embodiments, be pneumatically or electromagnetically activated.

Naturally Supernatant Buoy 218

Figure 20:
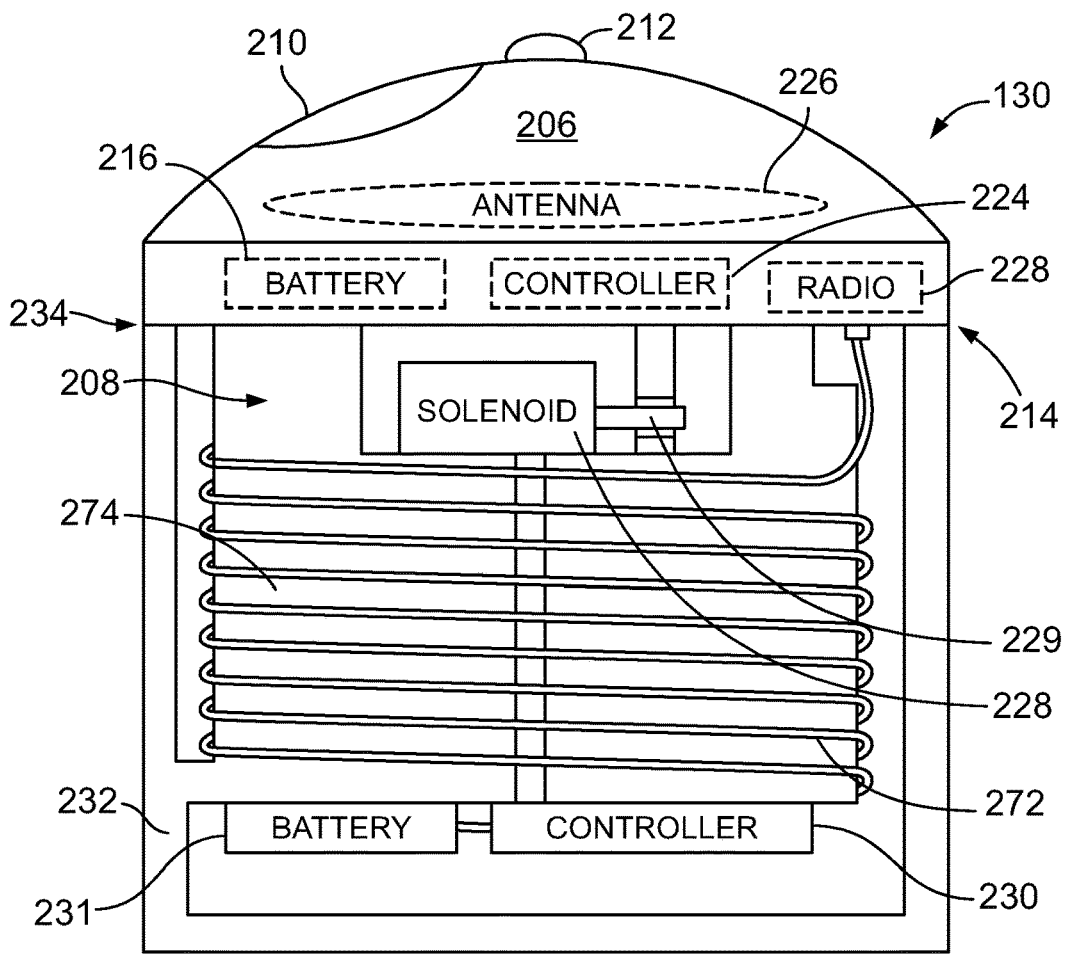
FIG. 20 illustrates an example of a naturally supernatant buoy and tether, in accordance with an example implementation.

Referring to the supernatant buoy 218 shown in FIGS. 20, 21 and 25, the buoy actuator is a solenoid 228. A spring locking pin 229 retains the buoy 218 the pin is retracted by the solenoid 228.

In one example embodiment, the buoy controller 224 and battery 216 control the activation of the solenoid 228, in addition to controlling the radio module 214, speaker 210, and light 212. In another example embodiment, the buoy 130 also includes a separate activation controller 230 and battery 231 to control the activation of the solenoid 228. The separate activation controller 230 and battery 231 are within a housing 232 near the buoy 218.

When a controller (either the buoy controller 224 or activation controller 230) receives a rescue deployment signal from the system controller 106, the solenoid 228 activates. The buoy 218 then separates from the housing 232 at the plane indicated by the reference number 234 in FIG. 20, and the buoy 218 is allowed to ascend toward the surface.

In an example embodiment, the naturally supernatant buoy 218 is generally rigid and, in large part, constructed of a material less dense than water (such as, for example, polystyrene or rubber). In an example embodiment shown in FIG. 21, the solenoid 228 holds the supernatant buoy onto to the BCD 112.

Inflatable Buoy 220

In an example embodiment, the inflatable buoy 220 includes the communication module 206 and an inflatable buoy portion, also referred to as a balloon 244. In one example embodiment, the buoy 220 is configured, when deflated, to be rolled up or packed so that the communication module 206 (antenna, light, and/or speaker) are wrapped within the inflatable portion 244 of buoy 220.

Figure 19:
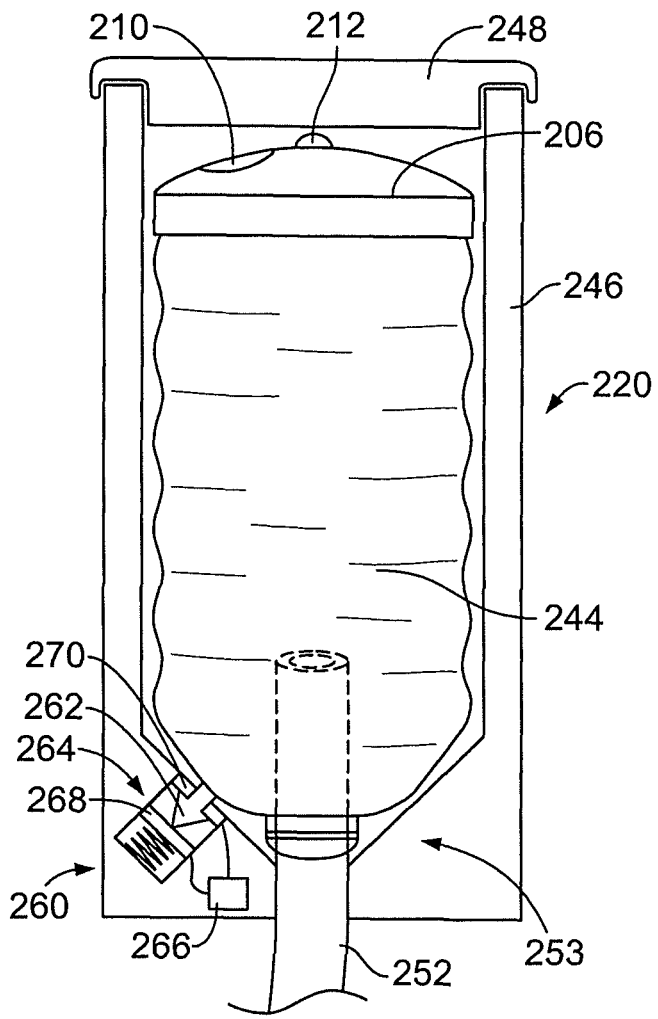
FIG. 19 illustrates an example of an inflatable buoy, in accordance with an example implementation.
Figure 24:
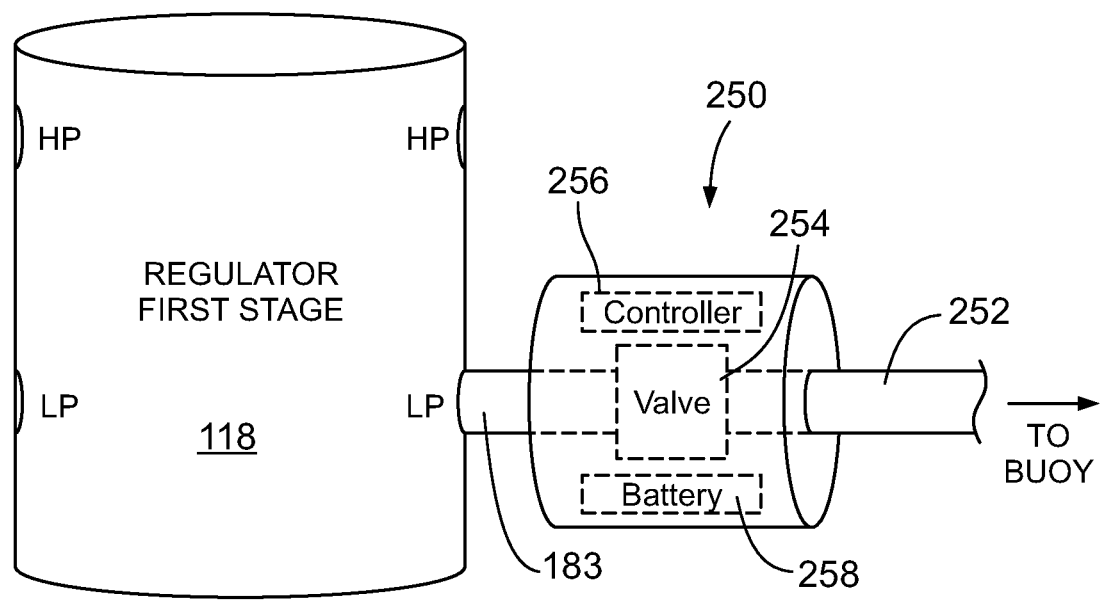
FIG. 24 illustrates an example diagram of a buoy fill valve in communication with the low pressure port of the first stage of a regulator, in accordance with an example implementation.
Figure 26:
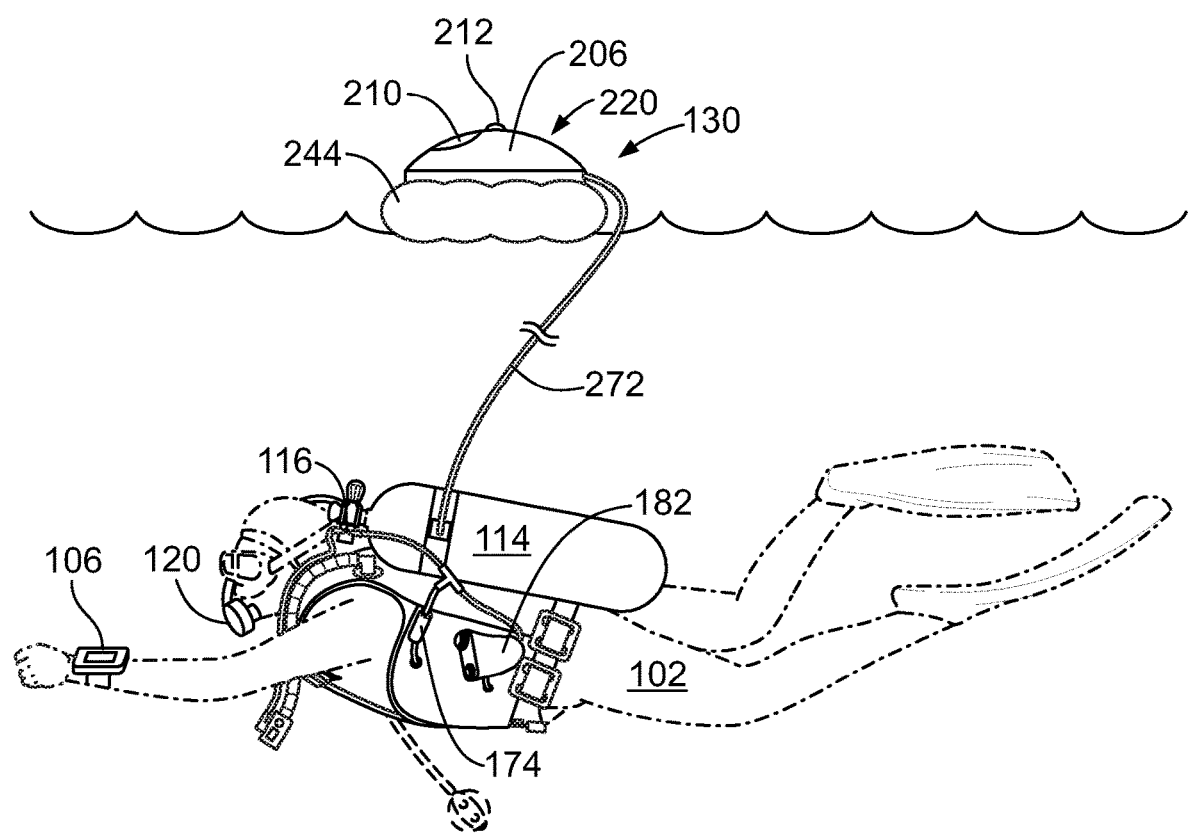
FIG. 26 illustrates an example of a floating, inflated, tethered buoy, in accordance with an example implementation.

In the example embodiments shown in FIGS. 19, 24, and 26, the communication module 206 is a rigid structure attached to the balloon 244. The uninflated balloon 244 is pressed in a generally rigid, tubular housing 246. A cap 248 is press fit onto an end of the housing 246, and a valve assembly 250 is in communication with the housing 246 via a fill stem 252. The balloon 244 may be constructed from, for example, a urethane plastic or polyethylene material. The housing 246 and cap 248 generally protect the inflatable buoy 220 (communication module 206 and balloon 244) against physical damage.

Referring to the example embodiment of FIG. 24, the valve assembly 250 includes a buoy fill valve 254, fill controller 256, and battery 258. The fill valve 254 is a waterproof, electrically-operated, normally-closed solenoid valve, powered by the battery 258, resting between the supply hose 183 and fill stem 252. The buoy fill valve 254 may be similar in general design to the BCD valve 174, albeit with only inlet and outlet ports.

The fill controller 256, also powered by the battery 258, receives a buoy rescue deployment signal from the controller 106 of the system 100 and responsively moves an internal member of the valve 254 to form a passageway between the low-pressure supply hose 183 and the fill stem 252, allowing pressurized gas from the hose 183 to flow into the fill stem 252 and enter the balloon 244.

Referring to the example embodiments of FIGS. 19, 22, 23, 24, and 26, upon receiving an emergency deployment signal, the valve 250 opens and allows gas from the tank 114 to inflate the balloon 244 and cause the buoy 220 to ascend. As shown in FIG. 19, a retainer mechanism (e.g., a collapsible seal 253, slip fit on the fill stem 252) keeps the balloon 244 in communication with the fill stem 252 until the balloon 244 is sufficiently inflated. As the balloon 244 inflates, it releases from the fill stem 252, and the collapsible seal 256 prevents escape of gas (e.g., air) from the balloon 244.

Figure 22:
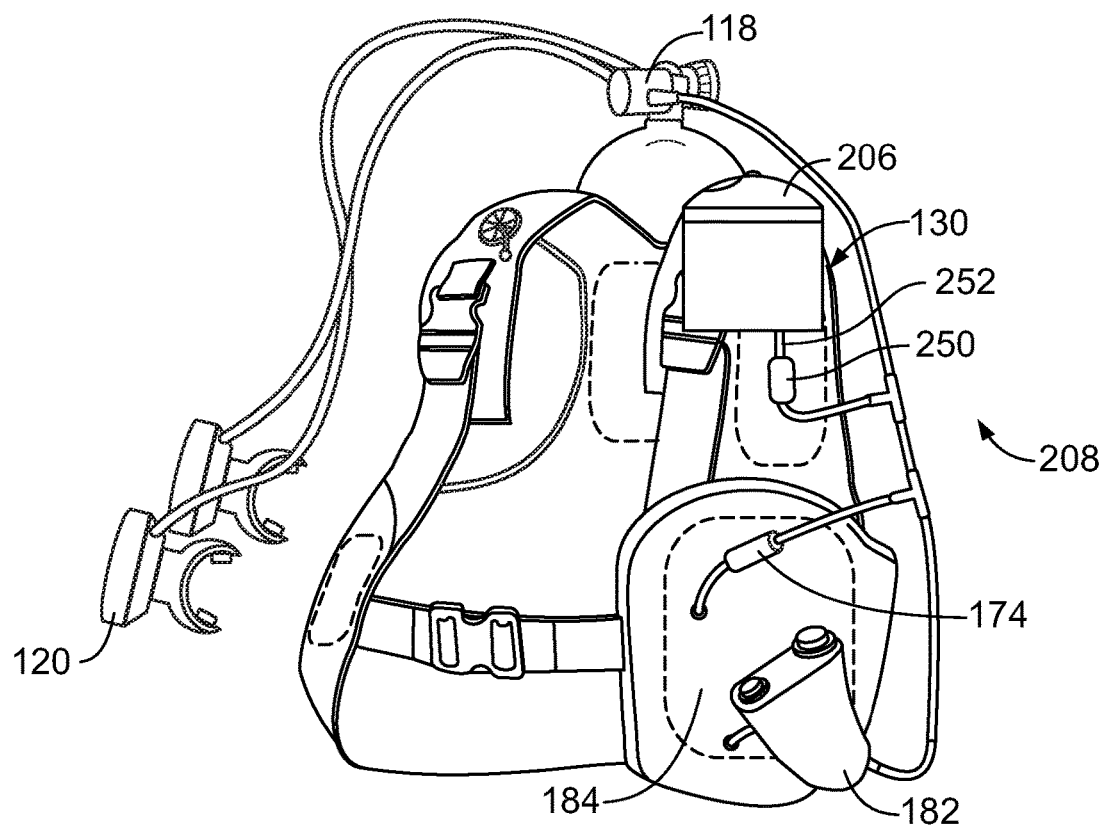
FIG. 22 illustrates an example of a BCD, inflatable buoy, and buoy fill valve, in accordance with an example implementation
Figure 23:
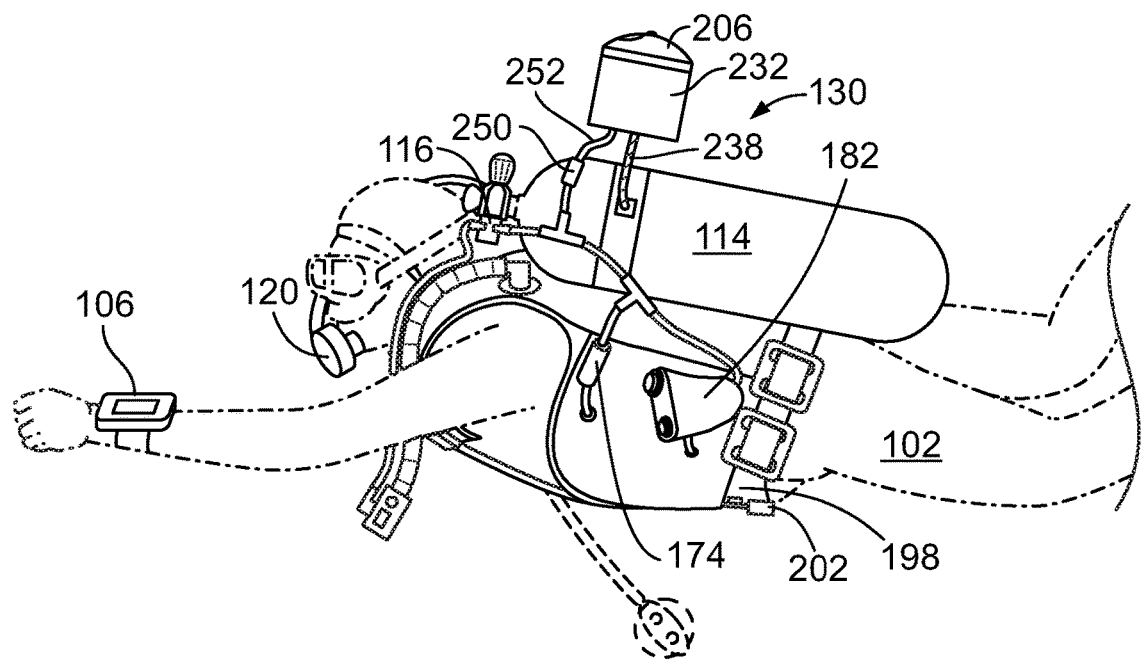
FIG. 23 illustrates an example of a tank, inflatable buoy and buoy fill valve, in accordance with an example implementation

In an example embodiment shown in FIG. 22, the fill tube 252 is attached to the BCD 112. In another example embodiment shown in FIG. 23, the fill tube 252 is attached to the tank 114. A short line 238, such as, e.g. a nylon rope, connects the supernatant buoy 218 to the tank 114. The tendency of the housing 246, cap 248, and balloon 244 to float generally keeps the communication module 206 oriented upward, toward the water surface.

In an example embodiment, the cap 248 is a press-fit seal, comprised of rubber or other compliant material. The communication module 206 of the buoy 220 presses against the cap 248 of the housing 246, pushing it off and clearing the way for the buoy 220 to ascend toward the surface. After a period of time, the air-fill controller 256 provides a signal to close the valve 254 and discontinue supplying gas to the fill balloon 244.

In another example embodiment, housing 246 further includes the retention assembly 260 having a rubber retention plug 262 and shutoff switch 264. The plug 262 retains the uninflated balloon 244 in the tubular housing 246 until the balloon 244 begins to inflate. Upon being inflated, the buoy 220 floats upward, out of the housing 246. When the retention plug 262 pulls from the housing 246 as a result of the balloon 244 inflating, the switch 264 closes, signaling (either via a wire or wirelessly) to the fill controller 256 close the valve 254 and discontinue allowing gas to flow to the fill stem 252. In an example embodiment, a sensor 266 detects that the contacts 268, 270 are in contact and sends a short-range RF signal to the controller 256, instructing it to close.

In another example embodiment, the buoy 220 includes a check valve matingly engaging a fill stem valve. A sensor module receives a buoy rescue deployment signal from the system controller 106, triggering the release of a clasp coupling the check valve and fill valve 254. The release of the clasp allows the buoy 220 to disconnect from the fill valve 254 and float toward the surface.

Buoy Tether 272

In some example embodiments, no tether is used. See FIGS. 21 and 25. Absent water current or other disruptions, the buoy 130, once released, typically reaches the water surface in the general location of the still-submerged diver 102.

In other example embodiments, however, the buoy subsystem 128 includes a tether 272 connected between the diver 102 and the buoy 130, such shown in FIGS. 20 and 26.

In the example embodiment shown in FIG. 20, the tether 272 is initially wrapped around a spool 274 within the housing 232 of the buoy 130. As the communication module 206 floats to the water surface, the tether 272 unwraps from the spool 274, and one end is brought to the surface by the buoy 130.

Referring to FIG. 26, when connected between a floating buoy 130 and diver 102, the tether 272 also helps maintain the floating buoy 130 in the vicinity of the submerged diver in distress. Should a rescue diver at the surface see the buoy 130 wish to descend to the diver in distress, the rescue diver can use the tether 272 as a guide to lead her to the stricken diver, even when visibility is poor (e.g., in murky water or at night).

Diver to Surface Communication

In one example embodiment, the tether 272 is a nonconductive line. In other example embodiments, however, the tether 272 comprises a wire, optical transmission cable, etc., for facilitating electronic communication with a submerged diver 102 and another person on the surface. For voice communication, the diver 102 wears an earphone/microphone assembly with a full-face mask 170, as shown in FIG. 10. The conductive tether 272 is interconnected to the radio 214 in the communication module 206 of the buoy 130. Using the tether 272 and radio 214, the diver 102 can talk, and listen, to people above the surface of water.

For example, a diver may be unable to come to the surface, or may simply prefer not to do so, while still wishing to communicate with others on the surface. In such a case, the diver may use the user interface 152 to release the buoy 130 with a conductive tether 272.

Safety Process

As described above, according to an example embodiment, the controller 106 is in communication with one or more sensors 104 (including in at least some embodiments, biological sensors), the alarm system 108, the user or diver-operable controls 159 (such as the Off button 162), the BCD control valve 174, and the buoy actuator 208. The BCD control valve 174 is connected to a supply of compressed gas (such as the tank 114), the BCD bladder 184, and a vent port 196.

Figure 27:
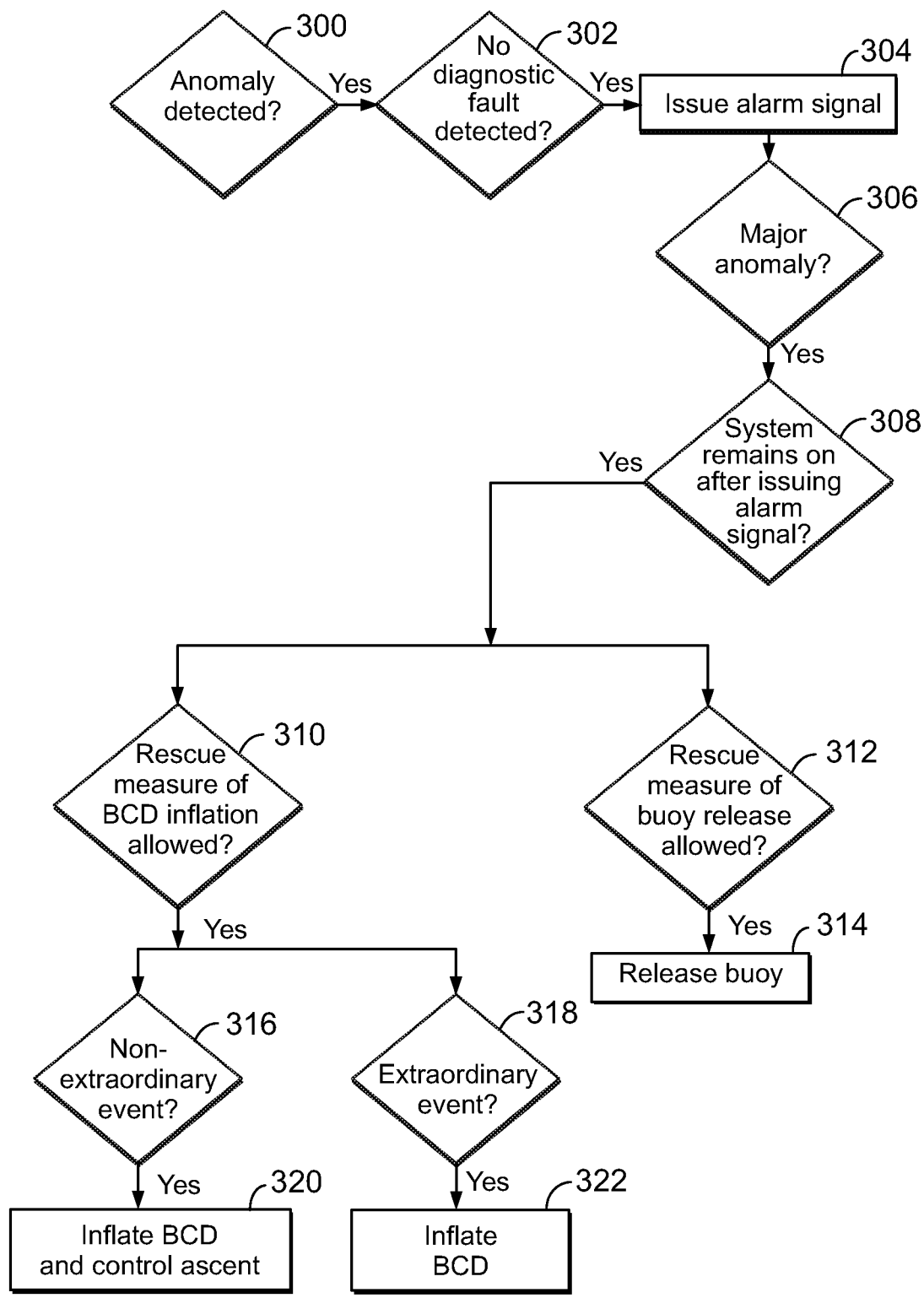
FIG. 27 illustrates an example of a process used by configuration of the safety system of FIG. 23, in accordance with an example implementation.

The controller 106 receives biological sensor data from one of the biological sensors. Referring to FIG. 27, the controller 106 determines, at Step 300, whether data from a sensor 104 indicates an anomalous parameter value. At Step 302, the controller 106 conducts a diagnostic check to determine whether any apparently anomalous parameter value results from a fault within the system 100. If an anomaly in a parameter value is detect and does not appear to be the result of a fault within the system 100, the controller 106, at Step 304, issue an alarm signal. The controller 106 issues a Caution alarm signal for a minor diver condition and a Warning alarm signal for a major (more serious) diver condition. An audible alarm 122 and/or light alarm 124 activate in response to the alarm signal.

Upon determining, at Step 306, that the parameter value correlates to a major anomaly (i.e., the sensor data are consistent with a serious diver condition), the controller 106 determines, at Step 308, whether the stop input has been operated for a time interval after issuing the alarm signal. If not, the controller 106 determines, at Steps 310 and 312, whether it is in a mode allowing the rescue measure of BCD inflation or the rescue measure of a buoy release or buoy. If a buoy release is allowed, the controller 106 issues, at Step 314, a buoy release signal, allowing the buoy 130 to ascend to the water surface.

If BCD inflation is allowed, the controller 106 determines, at Steps 316 and 318, whether the major anomaly is consistent with a non-extraordinary event or extraordinary event. If the anomaly corresponds to a non-extraordinary event (albeit a major anomaly), the controller 106 issues a BCD valve actuation signal at Step 320. This action causes the BCD valve 174 to open and allow pressurized gas to enter the bladder 184 of the BCD 112.

The controller 106 further determines its rate of ascent in the water and responsively varies the valve actuation signal, whereby the valve activation signal instructs the BCD valve 184 to put the inlet port 192 in communication with the outlet port 194 when the rate of ascent is below a minimum threshold, to close when the rate of ascent is within minimum and maximum thresholds; and to block the inlet port 192 and put the outlet port 196 in communication with and the vent port 196 when the rate of ascent is above a maximum threshold.

If the major anomaly is consistent with an emergency diver condition (such that the diver requires immediate help, despite the potential risks of ascending rapidly), the controller 106, at Step 322, opens the BCD valve 174. In such an emergency condition, the controller 106 does not keep the diver below a threshold rate of ascent.

The steps of FIG. 27 generally followed by an example embodiment of the system 100 need not necessarily be taken in the order presented, nor must every step necessarily be taken. For example, the step of conducting diagnostic test may be done continually (rather than once, as shown in FIG. 27) or may not be performed at all, particularly for a robust system.

In an example embodiment, the controller 106 includes a non-transitory, computer readable medium storing instructions. The controller 106 also includes at least one processor in communication with the computer-readable medium. When the processor(s) executes the stored instructions, the controller, a type of computing device, performs the operations attributed to the controller 106 in the above description.

CONCLUSION

The system 100 combines different monitoring solutions into one system. A diver can wear a single device that monitors both body parameters and system parameters. It can provide one or more alarms to summon help or bring an unconscious diver to the surface. More than one sensor can be placed around a diver's body and on the equipment, with the sensors 104 communicating with the controller 106, which can be central or distributed.

The system 100 may include one or more processors and data storage units, which together may be part of the controller 106. The system 100 may also include additional sensor(s), power source(s), mechanical components, and electrical components. The system 100 is shown for illustrative purposes, and may include more or fewer components. The various components of system 100 may be connected in any functioning manner, including wired or wireless connections. In some example embodiments, components of the system 100 may be distributed among multiple physical entities rather than a single physical entity.

The processor(s) of the controller 106 and/or sensors 104 may operate as one or more general-purpose hardware processors or special purpose hardware processors (e.g., digital signal processors, application specific integrated circuits, etc.). The processor(s) may be configured to execute computer-readable program instructions, and manipulate data, both of which are stored in the data storage. The processor(s) may also, directly or indirectly, interact with other components of the system 100, such as sensor(s), power source(s), mechanical components, and/or electrical components. The controller 106 may include one or more electrical circuits, units of digital logic, computer chips, and/or microprocessors configured to (possibly among other tasks), interface between any combination of the sensor(s), the power source(s), the electrical components, and the control system 100.

Further, in an example embodiment, the controller 106 includes a user (or diver) interface 152 between the system 100 and a diver 102 and/or other divers. The system 100 may perform operations for diving in addition to those described in this disclosure. Operations of the controller 106 may be carried out by one or more the processor(s) in one or more physical locations. During operation, the controller 106 may communicate with other systems carried by the diver 102 or by other divers or by equipment below, on, or above the water surface.

Further, the system 100 may include sensor(s) configured to receive information indicative of the state of the system 100, including sensor(s) that may monitor the state of the various components of the system 100. The data provided by the sensor(s) 104 may enable the system 100 to determine errors in operation as well as monitor overall operation of components of the system 100.

The arrangements described herein are for purposes of example only. As such, those skilled in the art will appreciate that other arrangements and other elements (e.g., interfaces, operations, orders, and groupings of operations, etc.) can be used instead, and some elements may be omitted altogether according to the desired results. Further, many of the elements that are described are functional entities that may be implemented as discrete or distributed components or in conjunction with other components, in any suitable combination and location.

While various aspects and implementations have been disclosed herein, other aspects and implementations will be apparent to those skilled in the art. The various aspects and implementations disclosed herein are for purposes of illustration and are not intended to be limiting, with the true scope being indicated by the following claims, along with the full scope of equivalents to which such claims are entitled. Also, the terminology used herein is for the purpose of describing particular implementations only, and is not intended to be limiting.

I claim:

1. An apparatus for a diver comprising:
a sensor configured to measure a biological parameter of the diver and transmit a sensor signal correlated to a biological parameter value;
a controller configured to receive the sensor signal, make a determination the biological parameter value correlated to the sensor signal is anomalous, and, in response to the determination, initiate an audible alarm, the controller further configured to categorize the anomalous biological parameter value as either:
a minor anomaly, where the value is outside a first range and consistent with the diver having an anomalous biological condition for which the diver is not at substantial risk absent assistance,
a major anomaly, where the value is outside a second range and consistent with the diver having an anomalous biological condition for which the diver is at substantial risk absent assistance, and
an emergency anomaly, where the value is outside a third range and consistent with the diver having an anomalous biological condition for which the diver is at imminent risk of a catastrophic event;
a diver-activatable input device configured to provide a stop signal upon being activated by the diver;
a timer, in communication with the diver-activatable input device, configured to:
begin measuring a time interval upon an initiation of the audible alarm,
detect the stop signal during the time interval, and
issue a rescue deployment signal when no stop signal is detected during the time interval;
the controller further configured to receive the rescue deployment signal and responsively issue a major anomaly alarm signal upon having categorized a major anomaly or an emergency alarm signal upon having categorized an emergency anomaly;
the controller further configured to determine a rate of ascent for the apparatus and responsively issue an ascent control signal; a buoyancy valve assembly having:
an inlet port connectable to a source of pressurized gas,
an outlet port connectable to a buoyancy bladder, and
a passageway between the inlet port and the outlet port
the buoyancy valve assembly, in communication with the controller, configured to:
respond to the major anomaly alarm signal and ascent control signal by responsively releasing gas into, and from, the bladder, for a controlled ascent of the diver, and
respond to the emergency alarm signal by responsively releasing gas into the bladder, for an unconstrained ascent of the diver.

2. An apparatus as claimed in claim 1 wherein the apparatus includes a wearable housing, and wherein the sensor and controller are substantially within the housing.

3. An apparatus as claimed in claim 2 wherein the biological parameter is a pulse of the diver.

4. An apparatus as claimed in claim 2 wherein the biological parameter is a blood oxygen level of the diver.

5. An apparatus as claimed in claim 2 wherein the biological parameter is a blood carbon monoxide level of the diver.

6. An apparatus for a diver with a weight belt comprising:
a sensor configured to measure a biological parameter of the diver and transmit a sensor signal correlated to a biological parameter value;
a controller configured to receive the sensor signal, make a determination the biological parameter value correlated to the sensor signal is anomalous, and, in response to the determination, initiate an audible alarm, the controller further configured to categorize the anomalous biological parameter value as either:
a minor anomaly, where the value is outside a first range and consistent with the diver having an anomalous biological condition for which the diver is not at substantial risk absent assistance,
a major anomaly, where the value is outside a second range and consistent with the diver having an anomalous biological condition for which the diver is at substantial risk absent assistance, and
an emergency anomaly, where the value is outside a third range and consistent with the diver having an anomalous biological condition for which the diver is at imminent risk of a catastrophic event;

a diver-activatable input device configured to provide a stop signal upon being activated by the diver;

a timer, in communication with the diver-activatable input device, configured to:

begin measuring a time interval upon an initiation of the audible alarm, detect the stop signal during the time interval, and issue a rescue deployment signal when no stop signal is detected during the time interval;

the controller further configured to receive the rescue deployment signal and responsively issue a major anomaly alarm signal upon having categorized a major anomaly or an emergency alarm signal upon having categorized an emergency anomaly;

a buckle actuator associated with the weight belt and in communication with the controller configured to disengage the weight belt from the diver in response to the emergency alarm signal;

the controller further configured to determine a rate of ascent for the apparatus and responsively issue an ascent control signal; a buoyancy valve assembly having:

an inlet port connectable to a source of pressurized gas, an outlet port connectable to a buoyancy bladder, and a passageway between the inlet port and the outlet port the buoyancy valve assembly, in communication with the controller, configured to:

respond to the major anomaly alarm signal and ascent control signal by responsively releasing gas into, and from, the bladder, for a controlled ascent of the diver, and respond to the emergency alarm signal by responsively releasing gas into the bladder, for an unconstrained ascent of the diver.

* * * * *